US008865404B2

(12) United States Patent
Wu et al.

(10) Patent No.: US 8,865,404 B2
(45) Date of Patent: Oct. 21, 2014

(54) METHODS FOR SEQUENCING NUCLEIC ACID MOLECULES

(75) Inventors: Chao-ting Wu, Brookline, MA (US); George M. Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 384 days.

(21) Appl. No.: 13/289,521

(22) Filed: Nov. 4, 2011

(65) Prior Publication Data

US 2012/0142540 A1 Jun. 7, 2012

Related U.S. Application Data

(60) Provisional application No. 61/410,411, filed on Nov. 5, 2010.

(51) Int. Cl.
*C12Q 1/68* (2006.01)
*C07H 21/00* (2006.01)

(52) U.S. Cl.
CPC .................................... *C12Q 1/6874* (2013.01)
USPC ........................................... 435/6.1; 536/22.1

(58) Field of Classification Search
USPC .................................. 435/6.1, 91.2; 536/22.1
See application file for complete search history.

(56) References Cited

U.S. PATENT DOCUMENTS

| | | | | |
|---|---|---|---|---|
| 4,849,336 | A | 7/1989 | Miyoshi et al. | |
| 5,198,537 | A | 3/1993 | Huber et al. | |
| 5,317,097 | A * | 5/1994 | Miller et al. | 536/24.31 |
| 5,344,757 | A | 9/1994 | Holtke et al. | |
| 5,354,657 | A | 10/1994 | Holtke et al. | |
| 5,356,776 | A * | 10/1994 | Kambara et al. | 435/6.12 |
| 5,700,642 | A | 12/1997 | Monforte et al. | |
| 5,702,888 | A | 12/1997 | Holtke et al. | |
| 5,739,386 | A | 4/1998 | Holmes | |
| 5,830,655 | A | 11/1998 | Monforte et al. | |
| 8,021,841 | B1 * | 9/2011 | Schatz | 435/6.1 |
| 2003/0186226 | A1 | 10/2003 | Brennan et al. | |
| 2003/0198974 | A1 * | 10/2003 | Cole et al. | 435/6 |
| 2004/0106728 | A1 | 6/2004 | McGall et al. | |
| 2004/0115719 | A1 * | 6/2004 | Horio et al. | 435/6 |
| 2009/0018024 | A1 | 1/2009 | Church et al. | |
| 2009/0035777 | A1 * | 2/2009 | Kokoris et al. | 435/6 |

FOREIGN PATENT DOCUMENTS

WO 1997/017160 A1 11/1991

OTHER PUBLICATIONS

Washizu, M. DNA manipulation in electrostatic fields. 7th Internal conference on Miniaturized chemical and biochemical analysis systems (Oct. 2003).*
Amsden, et al., "Rapid Nanoimprinting of Silk Fibroin Films for Biophotonic Applications," Adv. Mater., 2010, 22, 1746-1749.
Douglas, et al., "Rapid Prototyping of 3D DNA-Origami Shapes with caDNAno," Nucleic Acids Research, 2009, vol. 37, No. 15, 5001-5006.
Hertzberg, et al., "Cleavage of DNA with Methidiumpropyl-EDTA-Iron(II): Reaction Conditions and Product Analyses," Biochemistry, 1984, 23, 3934-3945.
Joshi, et al., "Chemical Cleavage of Plasmid DNA by Cu(II), Ni(II) and Co(III) Desferal Complexes," Biochemical and Biophysical Research Communications, vol. 182, No. 2, Jan. 31, 1992, 588-592.
Meunier, Bernard, "Metalloporphyrins as Versatile Catalysts for Oxidation Reactions and Oxidative DNA Cleavage," Chem. Rev., 1992, 1411-1456.
Pon, Richard T., "Solid-Phase Supports for Oligonucleotides Synthesis," Methods in Molecular Biology, vol. 20, Chapter 19, 1993.
Reed, et al., "Chemical Cleavage of Plasmid DNA by Glutathione in the Presence of Cu(II) Ions," Biochem. J. (1991), 275, 601-608.
Reich, et al., "A Whole-Genome Admixture Scan Finds a Candidate Locus for Multiple Sclerosis Susceptibility," Nature Genetics, vol. 37, No. 10, Oct. 2005.
Roberts, et al., "Rebase-Enzymes and Genes for DNA Restriction and Modification," Nucleic Acids Research, 2007, vol. 35, D269-D270.
Schultz, et al., "Single-Molecule Analysis Reveals Changes in the DNA Replication Program for the POU5F1 Locus Upon Human Embryonic Stem Cell Differentiation," Molecular and Cellular Biology, Sep. 2010, vol. 30, No. 18, 4521-4534.
Shoaib, et al., "Multiple Displacement Amplification for Complex Mixtures of DNA Fragments," BMC Genomics, 2008, 9: 415.
Swaminathan, et al., "Restriction Generated Oligonucleotides Utilizing the Two Base Recognition Endonuclease CviJI," Nucleic Acids Research, 1994, vol. 22, No. 8, 1470-1475.
Verma, et al., "Modified Oligonucleotides: Synthesis and Strategy for Users," Annu. Rev. Biochem., 1998, 67:99-134.
Zhang, et al., "Sequencing Genomes from Single Cells by Polymerase Cloning," Nature Biotechnology, vol. 24, No. 6, Jun. 2006.
Zhang, et al., "Long-Range Polony Haplotyping of Individual Human Chromosome Molecules," Nature Genetics, vol. 38, No. 3, Mar. 2006.

* cited by examiner

*Primary Examiner* — Ethan C Whisenant
(74) *Attorney, Agent, or Firm* — Banner & Witcoff, Ltd.

(57) ABSTRACT

Methods and compositions for determining the nucleic acid sequence of polynucleotides that are at least 1500 nucleotides in length are provided.

25 Claims, 17 Drawing Sheets

METHODS FOR SEQUENCING NUCLEIC ACID MOLECULES

RELATED APPLICATION DATA

This application claims priority to U.S. Provisional Patent Application No. 61/410,411, filed on Nov. 5, 2010 and is hereby incorporated herein by reference in its entirety for all purposes.

STATEMENT OF GOVERNMENT INTERESTS

This invention was made with government support under GM085169 and HG003170 awarded by the National Institutes of Health. The government has certain rights in the invention.

BACKGROUND

1. Field of the Invention

Embodiments of the present invention relate in general to methods and compositions for sequencing nucleic acid molecules.

2. Description of Related Art

Current sequencing strategies are unable to address many regions of large, complex genomes because of the size and sequence composition of such regions. The longest published DNA sequencing read lengths are about 1000 base pairs (bp) (ABI/Sanger capillary methods, and Roche FLX platforms). Such read lengths are not long enough to span the longest gaps in the human (and many other) genomes, which range up to 34 Mbp and include about 7% of the human genome. These gaps are likely to contain regions of medical significance (e.g., multiple sclerosis (Reich et al. (2005) Nat. Genet. 37(10):1113)).

One strategy that has been considered for addressing gaps in genomic sequences calls for subcloning the regions in question prior to sequencing. There are methods to subclone fragments that are on the order of 100 kb in length (bacterial artificial chromosomes (BACs) and Complete Genomics Long Fragment Read (CGI LFR)). However, fragments of this length 1) are long enough that they pose internal assembly problems, 2) are short enough that they don't span the aforementioned gaps, and 3) introduce amplification artifacts (in vivo or in vitro) more frequently than do smaller fragments. Alternative methods that have been considered utilize haplotyping by either in situ sequencing (Zhang et al. (2006) *Nat. Biotech.* 24(6):680) or dilution amplification (Zhang K (2006) Nat. Genet. 38(3):382), but such methods cannot fill long gaps.

SUMMARY

Current sequencing strategies are unable to determine the nucleotide sequences of many regions of large, complex polynucleotides, e.g., of genomes, because of the size and/or sequence compositions of such regions. Accordingly, the present invention provides novel methods and compositions to determine the nucleotide sequences of large polynucleotides, e.g., genomes, that have been intractable to sequencing. Accordingly, the present invention provides methods and compositions to sequence large and/or complex nucleic acid sequences (e.g., DNA and/or RNA sequences) using a method of arranging oligonucleotide sequences nearly linearly and parallel to one another on a substrate and the cleaving the oligonucleotides along a line perpendicular to the linearly arranged oligonucleotides. According to certain embodiments, these method steps may be referred to as a "bind and snap" method.

In certain exemplary embodiments, methods of determining the nucleic acid sequence of a polynucleotide that is at least 1500 nucleotides in length or greater are provided. The methods include the steps of providing a polynucleotide, cleaving the polynucleotide into a plurality of oligonucleotide sequences, immobilizing one end of each of the plurality of oligonucleotide sequences on a substrate, arranging the plurality of oligonucleotide sequences substantially linearly on the substrate, attaching a label (e.g., a barcode sequence) to a non-immobilized end of each of the plurality of oligonucleotide sequences, cleaving the plurality of oligonucleotide sequences at a cleavage line perpendicular to said plurality of oligonucleotide sequences to generate a plurality of labelled oligonucleotide fragments, collecting the plurality of oligonucleotide fragments, sequencing the plurality of oligonucleotide fragments to obtain oligonucleotide reads, assembling the oligonucleotide reads, and determining the nucleic acid sequence of the assembled oligonucleotide reads to determine the nucleic acid sequence of the polynucleotide.

In certain aspects, the steps of attaching, cleaving the plurality of oligonucleotide sequences, and collecting are repeated. In other aspects, the plurality of oligonucleotide fragments obtained from each collecting step are pooled. In yet other aspects, the plurality of oligonucleotide fragments obtained from each collecting step are kept separate from one another. In still other aspects, the methods include the step of amplifying the collected oligonucleotide fragments (e.g., by PCR, linear rolling circle amplification (RCA), hyperbranched RCA and any combinations of these). In certain aspects, the polynucleotide is at least about 2000 base pairs, at least about 5000 base pairs, or between about 5000 base pairs and about 34,000 base pairs in length. In other aspects, the polynucleotide is DNA or a portion of a genome. In yet other aspects, the portion of a genome includes one or more genomic gaps. In other aspects, the methods include the step of partially detaching the plurality of oligonucleotide sequences after they are immobilized.

In certain exemplary embodiments, methods of determining the nucleic acid sequence of a polynucleotide that is at least 1500 nucleotides in length are provided. The methods include the steps of providing a polynucleotide, cleaving the polynucleotide into a plurality of oligonucleotide sequences, immobilizing one end of each of the plurality of oligonucleotide sequences on a substrate, partially detaching the plurality of oligonucleotide sequences, arranging the plurality of oligonucleotide sequences substantially linearly on the substrate, attaching a label to a non-immobilized end of each of the plurality of oligonucleotide sequences, cleaving the plurality of oligonucleotide sequences at a cleavage line substantially perpendicular to said plurality of oligonucleotide sequences to generate a plurality of labelled oligonucleotide fragments, collecting the plurality of oligonucleotide fragments, sequencing the plurality of oligonucleotide fragments to obtain oligonucleotide reads, assembling the oligonucleotide reads, and determining the nucleic acid sequence of the assembled oligonucleotide reads to determine the nucleic acid sequence of the polynucleotide. In certain aspects, the partially detaching step is performed by contacting one or more of the plurality of oligonucleotide sequences with one or any combination of an endonuclease, a chemical, light, heat or a blade.

In certain exemplary embodiments, methods of determining the nucleic acid sequence of a polynucleotide that is at least 1500 nucleotides in length are provided. The methods include the steps of providing a polynucleotide, cleaving the polynucleotide into a plurality of oligonucleotide sequences, immobilizing one end of each of the plurality of oligonucleotide sequences on a substrate, arranging the plurality of oligonucleotide sequences substantially linearly on the substrate, attaching a barcode sequence to a non-immobilized end of each of the plurality of oligonucleotide sequences, cleaving the plurality of oligonucleotide sequences at a cleavage line substantially perpendicular to said plurality of oligonucleotide sequences to generate a plurality of labelled oligonucleotide fragments, collecting the plurality of oligonucleotide fragments, repeating the steps of attaching, cleaving the plurality of oligonucleotide sequences, and collecting, sequencing the plurality of oligonucleotide fragments to obtain oligonucleotide reads, assembling the oligonucleotide reads, and determining the nucleic acid sequence of the assembled oligonucleotide reads to determine the nucleic acid sequence of the polynucleotide. In certain aspects, a unique barcode sequence is used for each attaching step, and each repeat of the attaching step uses a different unique barcode sequence. In other aspects, a single barcode sequence is used for all attaching steps, and each repeated collection of oligonucleotide fragments is kept separate from the other collections of oligonucleotide fragments. In yet other aspects, a unique barcode sequence is used for each oligonucleotide sequence, and for all attaching steps. In other aspects, the steps of attaching, cleaving the plurality of oligonucleotide sequences, and collecting are repeated until substantially all of the plurality of oligonucleotide sequences have been cleaved into oligonucleotide fragments.

Further features and advantages of certain embodiments of the present invention will become more fully apparent in the following description of the embodiments and drawings thereof, and from the claims.

BRIEF DESCRIPTION OF THE DRAWINGS

The foregoing and other features and advantages of the present invention will be more fully understood from the following detailed description of illustrative embodiments taken in conjunction with the accompanying drawings in which.

DETAILED DESCRIPTION

Figure 1:
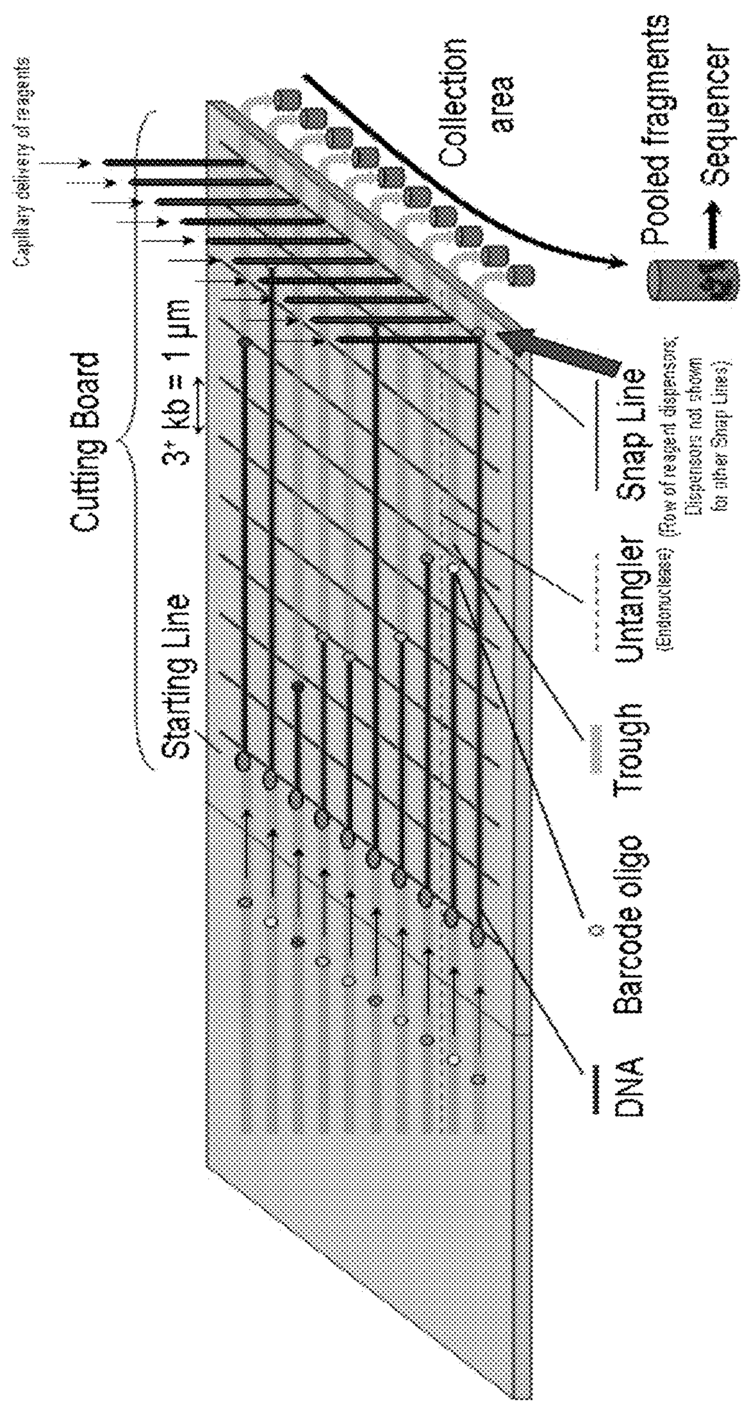
FIG. 1 schematically depicts an overview of a bind and snap method according to certain exemplary embodiments of the present invention. The following protocol can be used: 1) isolate one or more polynucleotides; 2) attach oligonucleotide sequences to a substrate (e.g., a cutting board), maximizing the chance of only one attachment per trough at the starting line; 3) partially detach oligonucleotide sequences; 4) activate cleavage lines, wash, end-label bound oligonucleotide sequences (e.g., with barcode sequences), then activate the next cleavage line; 5) collect oligonucleotide fragments, optionally pool, amplify and sequence; 6) optionally repeat cycles of barcoding, cleaving and collecting (pooling/amplifying).
Figure 2:
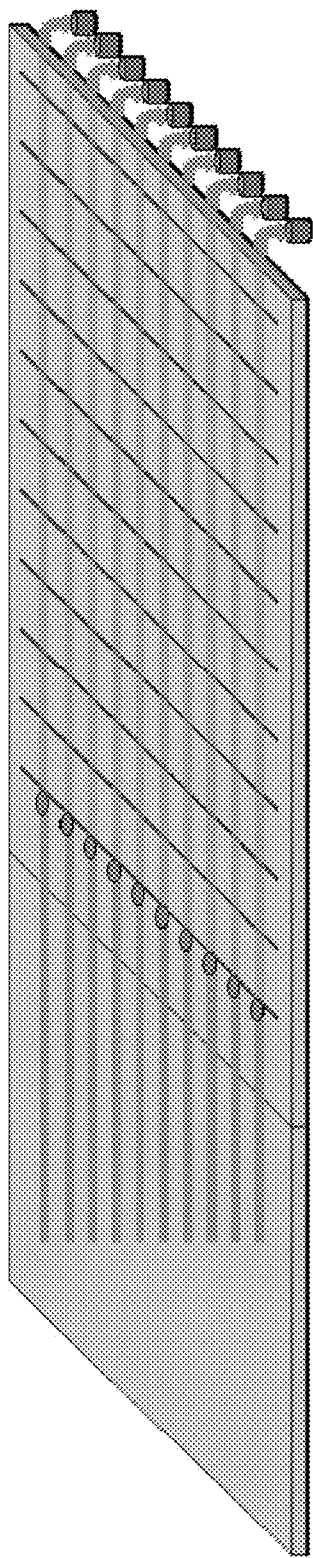
FIG. 2 schematically depicts a substrate on which oligonucleotide sequences are to be immobilized at one end and then arranged linearly and substantially parallel to one another in preparation for cleaving the oligonucleotides along a cleavage line. This substrate may be referred to as a "cutting board."
Figure 3:
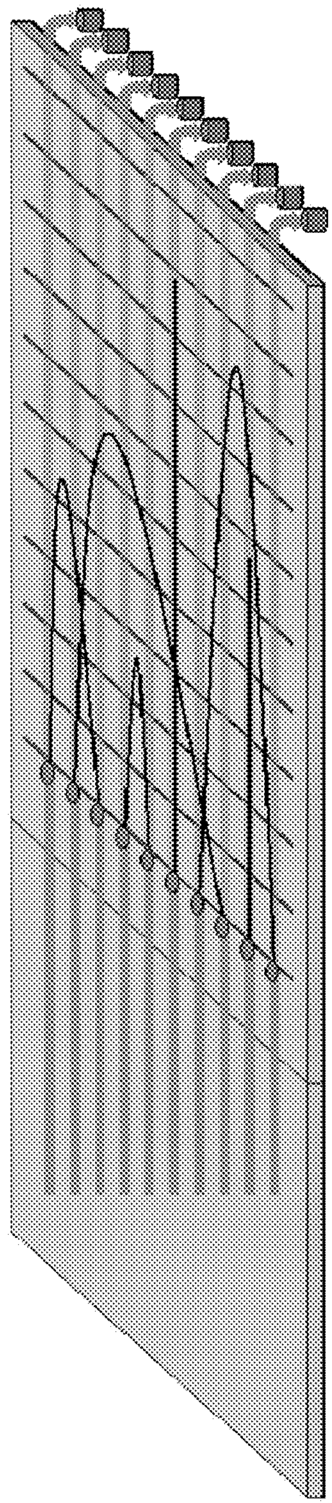
FIG. 3 schematically depicts the addition of oligonucleotide sequences to the cutting board.
Figure 4:
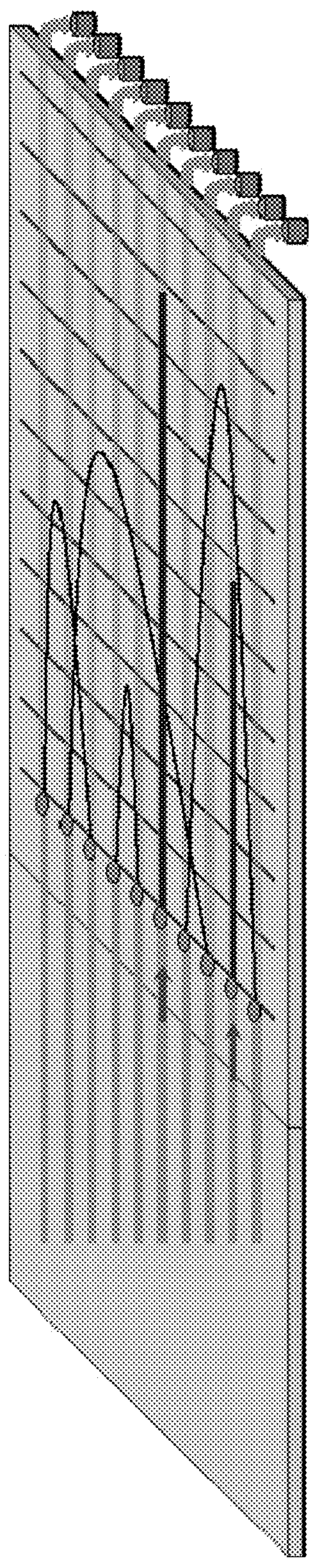
FIG. 4 schematically depicts two oligonucleotide sequences that are attached by only one end (red arrows) and are, therefore, not entangled.
Figure 5:
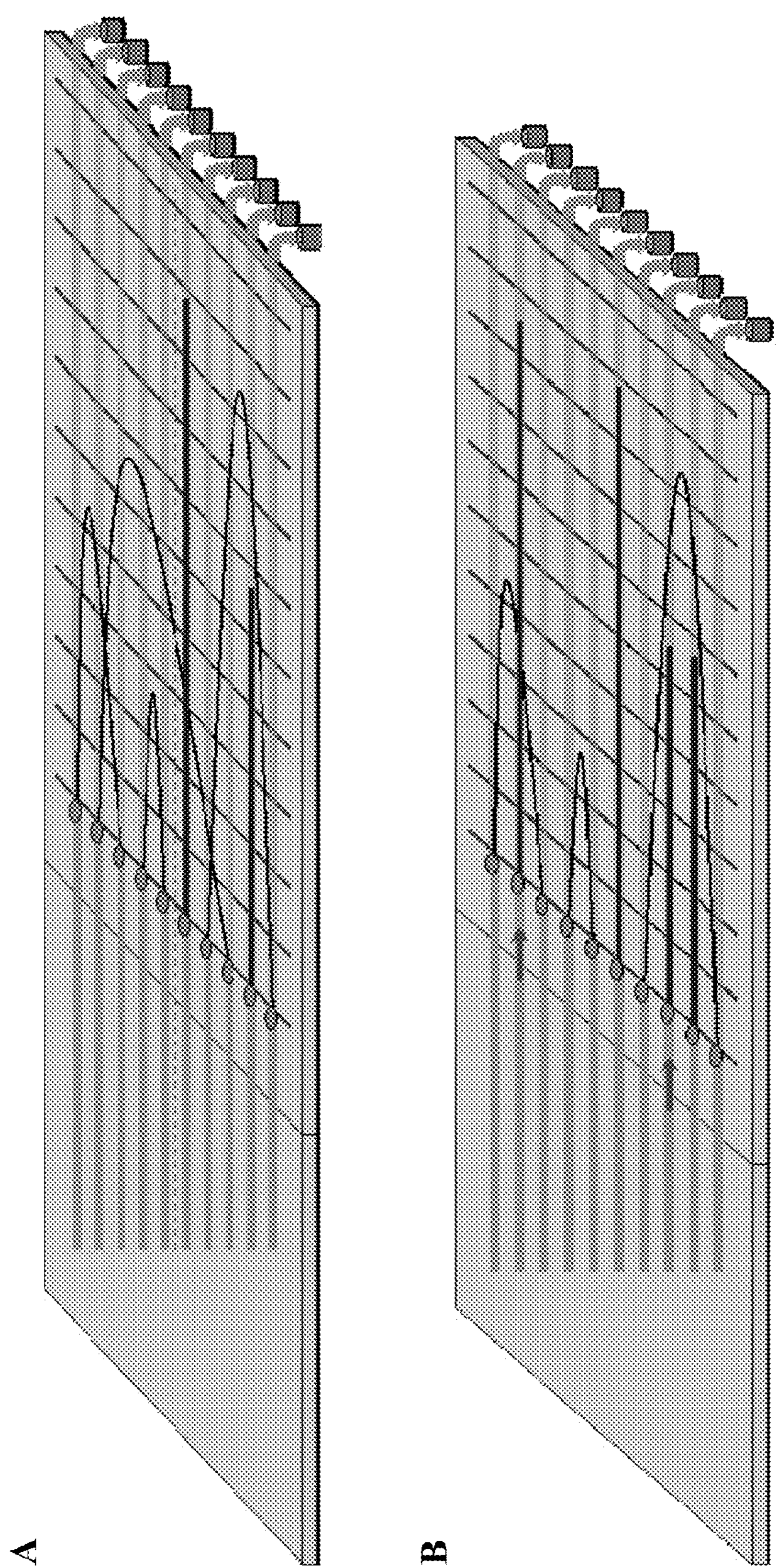
FIGS. 5A-5G schematically depict partial detaching of attached oligonucleotide sequences. (A) The central cleavage agent is activated (dashed line). (B) Two additional oligonucleotide sequences are partially detached (arrows). (C) Two additional cleavage agents are activated (dashed lines). (D) Two more oligonucleotide sequences are partially detached (arrows). (E) Four additional cleavage agents are activated (dashed lines). (F) Four more oligonucleotide sequences (e.g., DNA fragments) are partially detached (arrows). (G) Two additional cleavage agents are activated (dashed lines).
Figure 5:
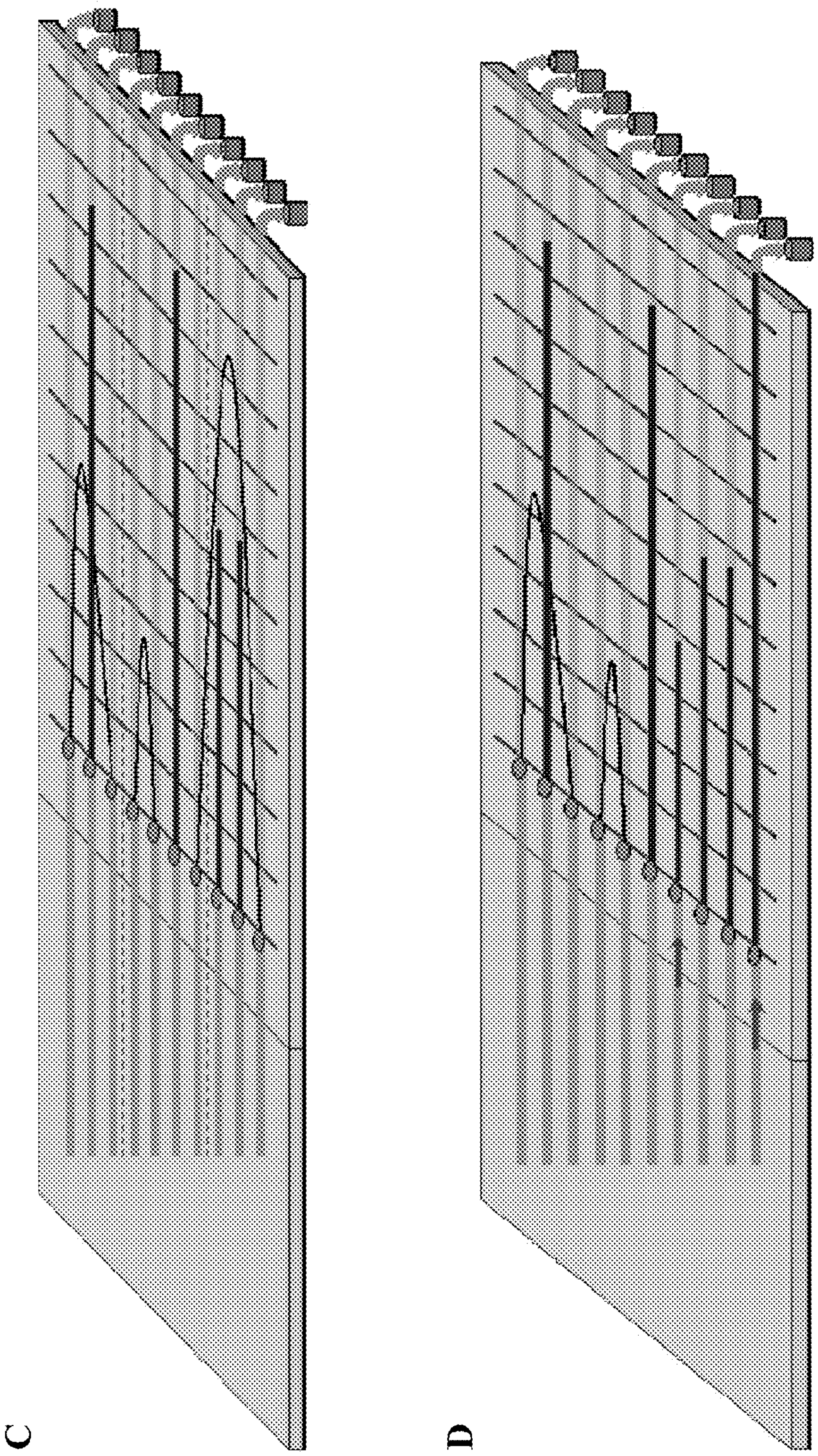
Figure 5:
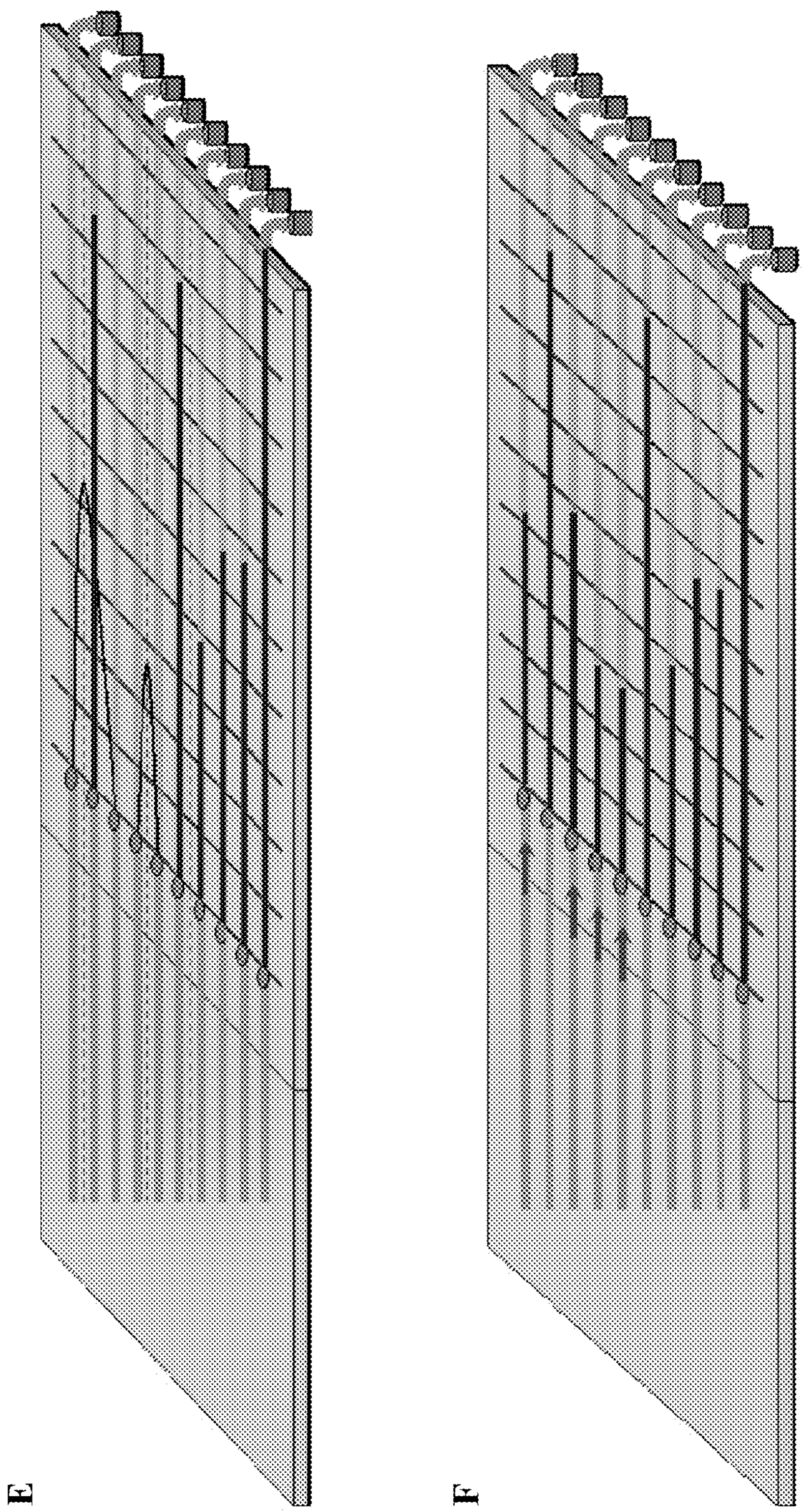
Figure 5:
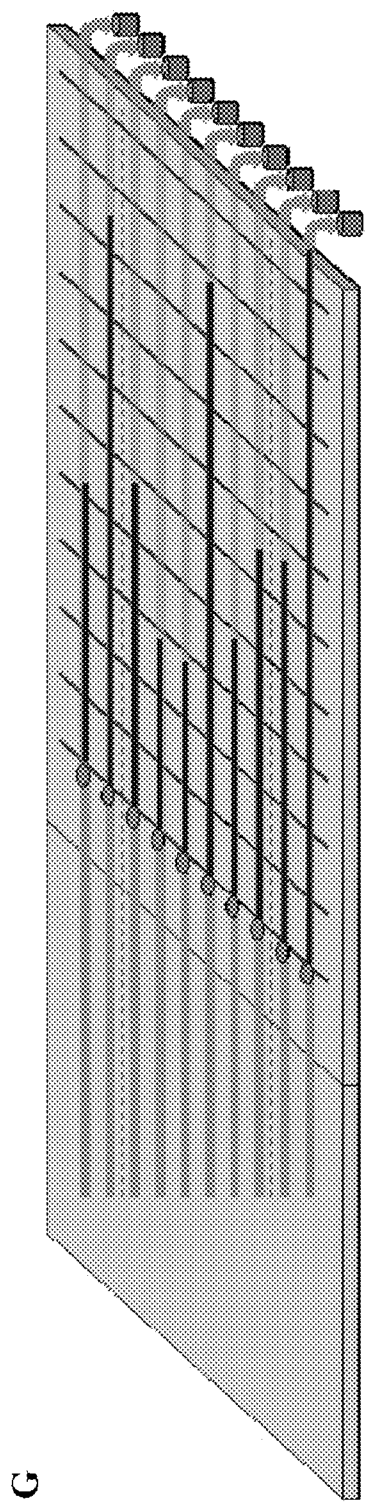
Figure 6:
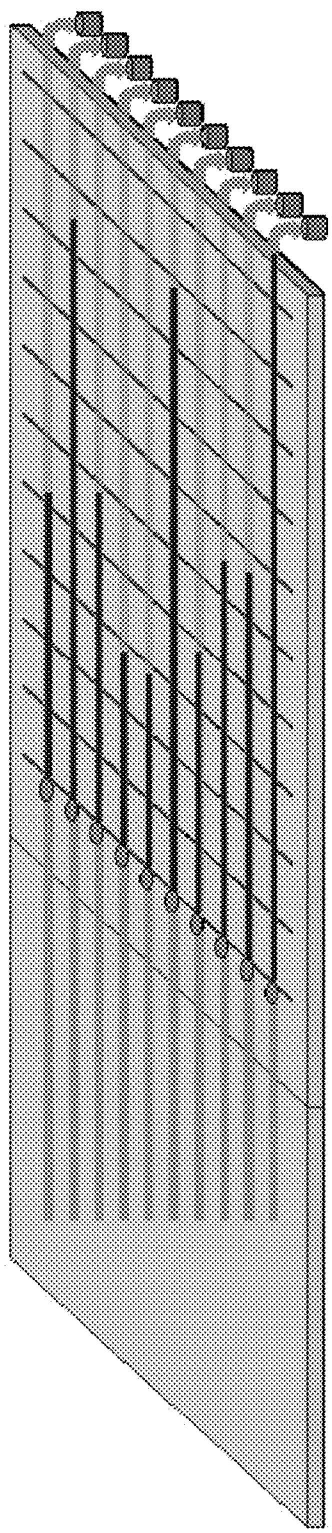
FIG. 6 schematically depicts each oligonucleotide sequence attached at only one end to the start line.
Figure 7:
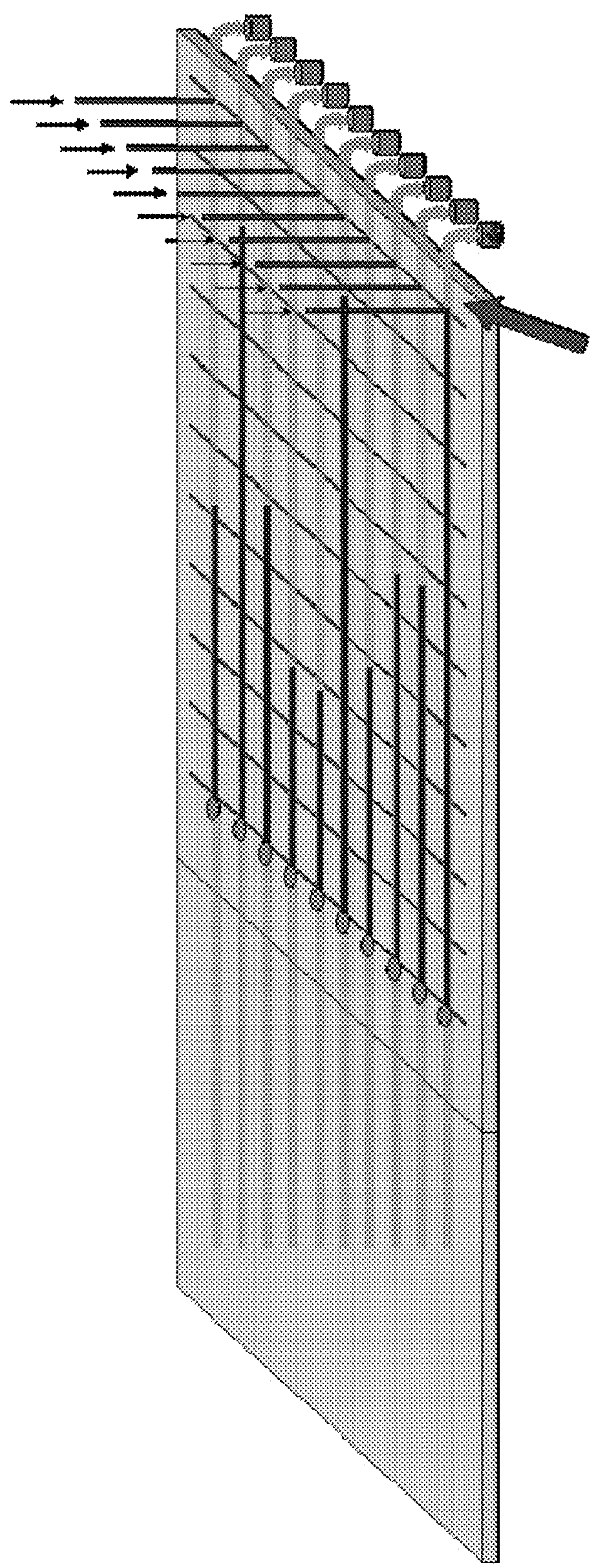
FIG. 7 schematically depicts activation of the cleavage line (red arrow). Upon activation, any oligonucleotide sequences (e.g., DNA) crossing the cleavage line are cleaved.
Figure 8:
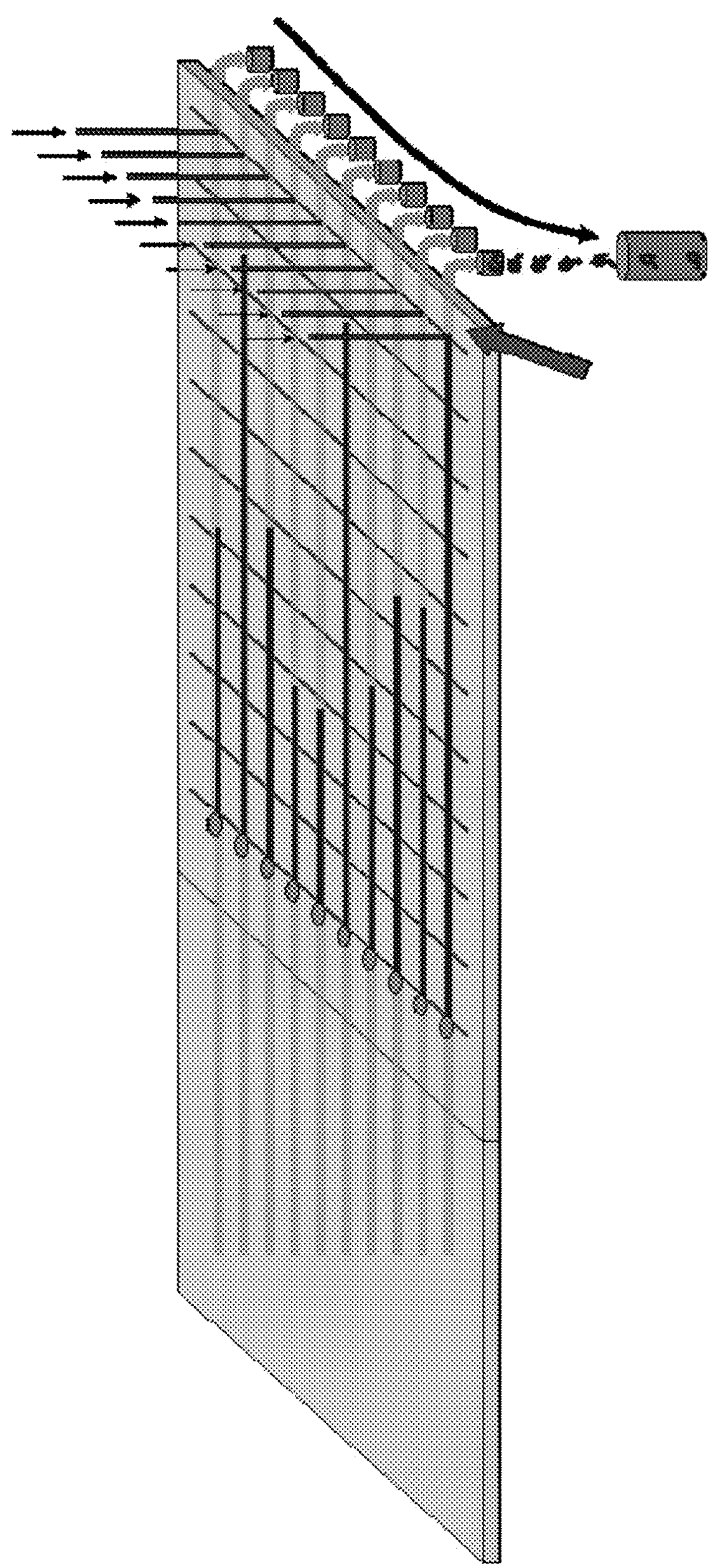
FIG. 8 schematically depicts collecting, pooling and discarding the released oligonucleotide (e.g., DNA) fragments.
Figure 9:
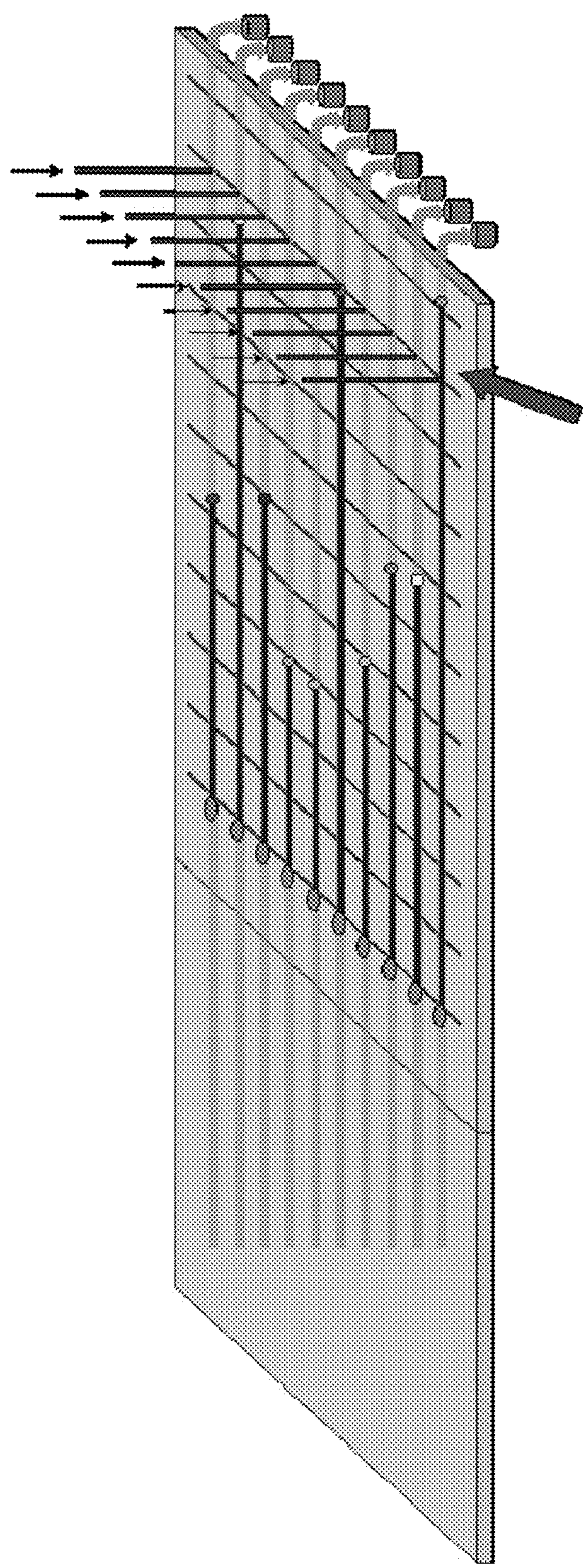
FIG. 9 schematically depicts attaching barcode sequences to all unbound oligonucleotide sequence ends (colored circles) followed by activation of the next cleavage line (red arrow).
Figure 10:
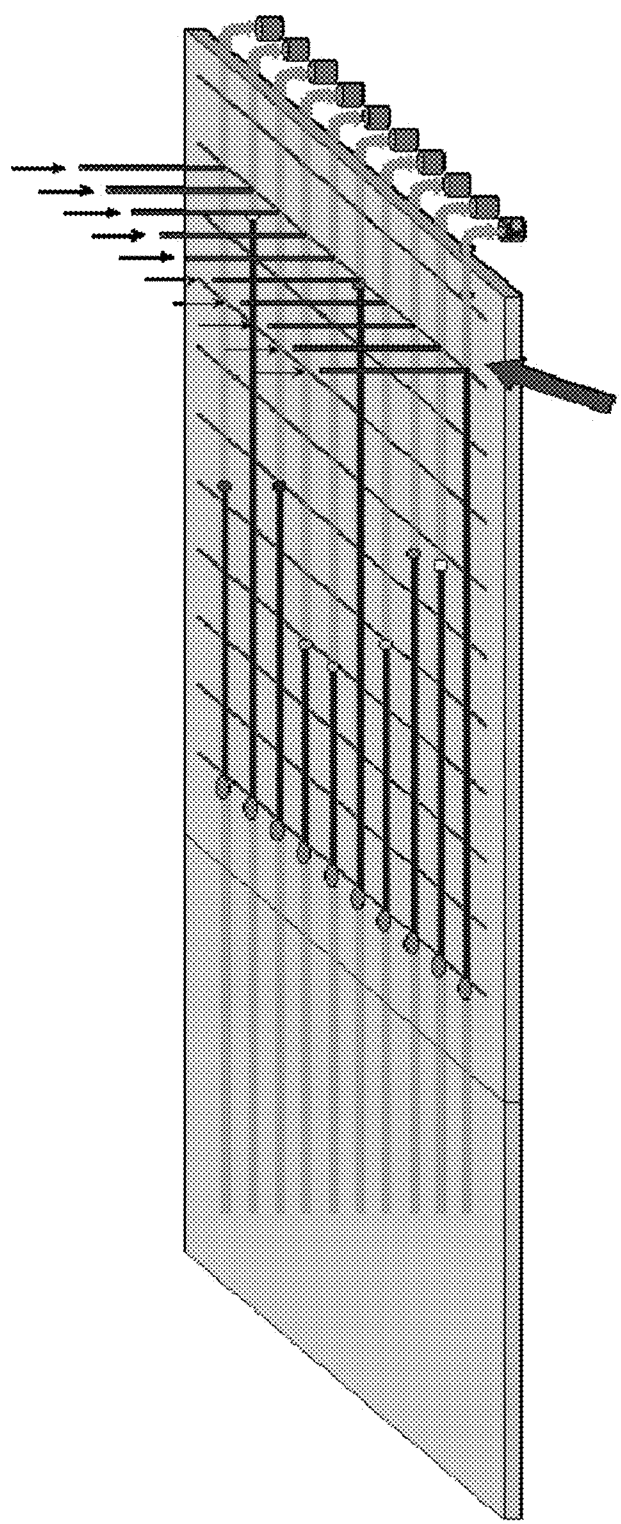
FIG. 10 schematically depicts collection of the released oligonucleotide fragments (e.g., DNA fragments).
Figure 11:
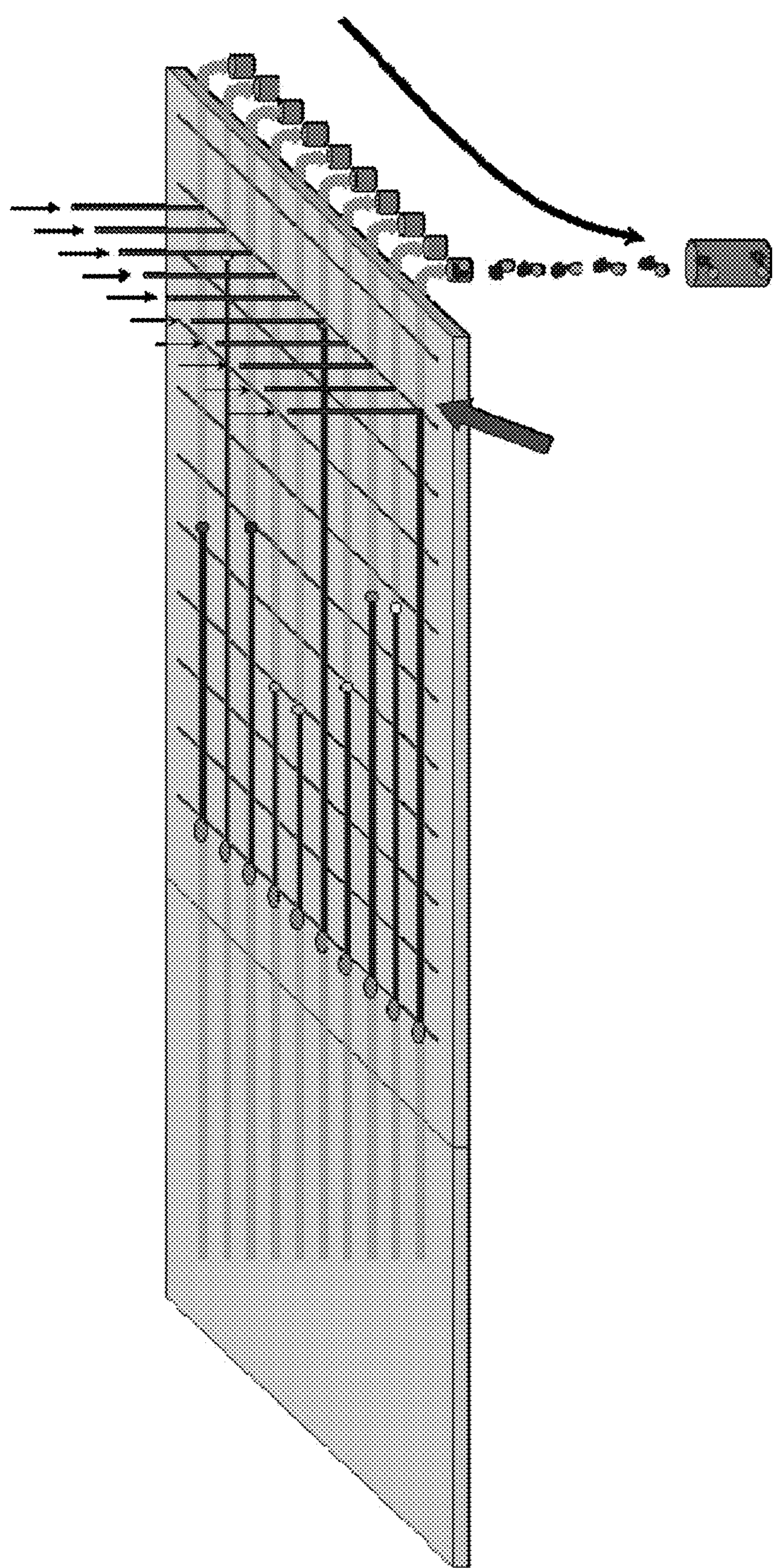
FIG. 11 schematically depicts pooling, amplification and sequencing of the released oligonucleotide fragments.
Figure 12:
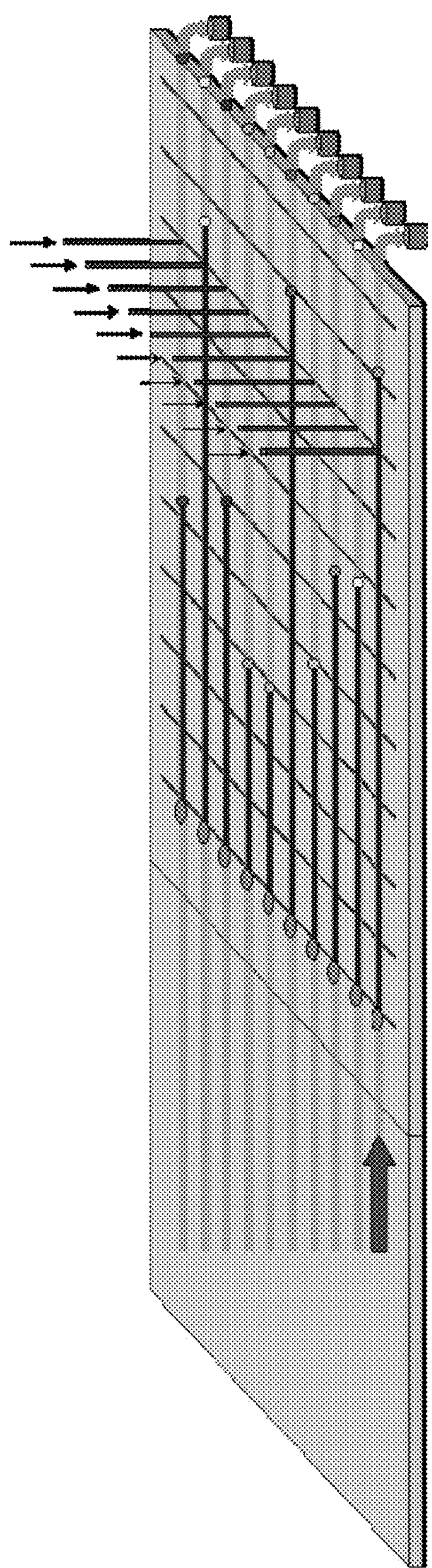
FIG. 12 schematically depicts attaching new labels (e.g., barcode sequences) to all free oligonucleotide sequence ends followed by activation of the next cleavage line.
Figure 13:
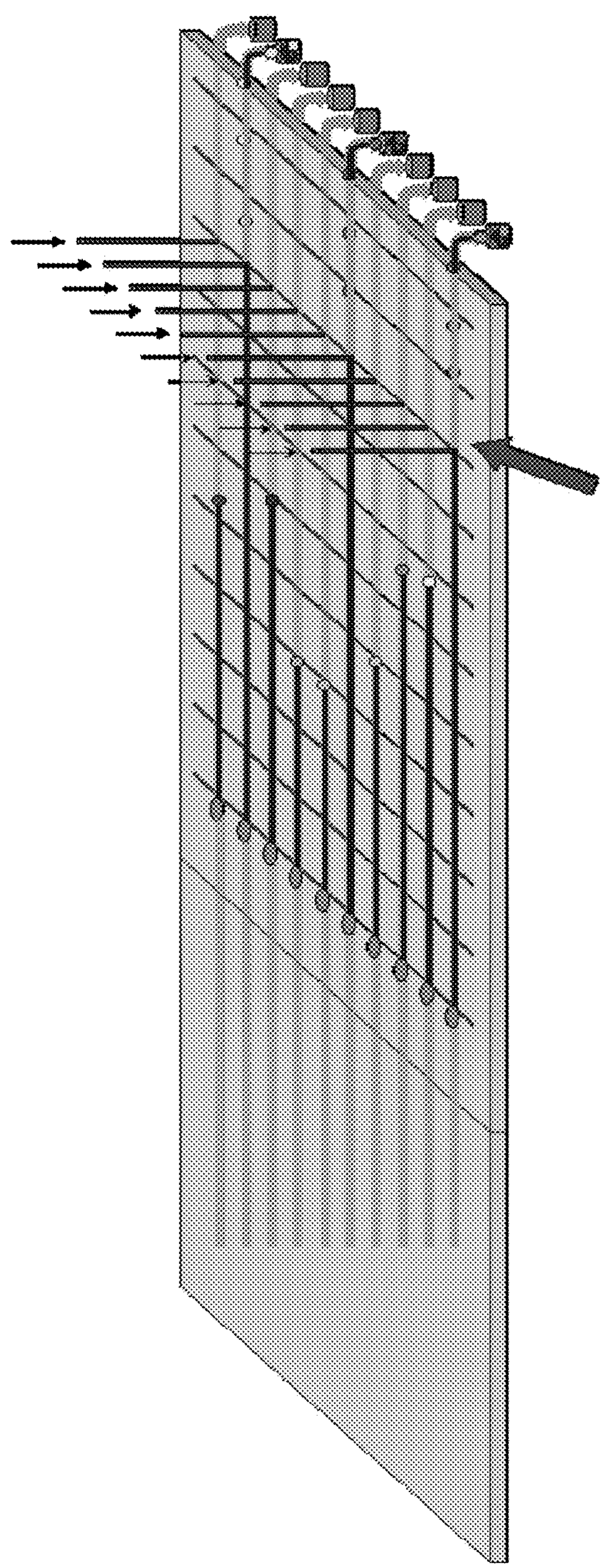
FIG. 13 schematically depicts collection of the released oligonucleotide fragments.
Figure 14:
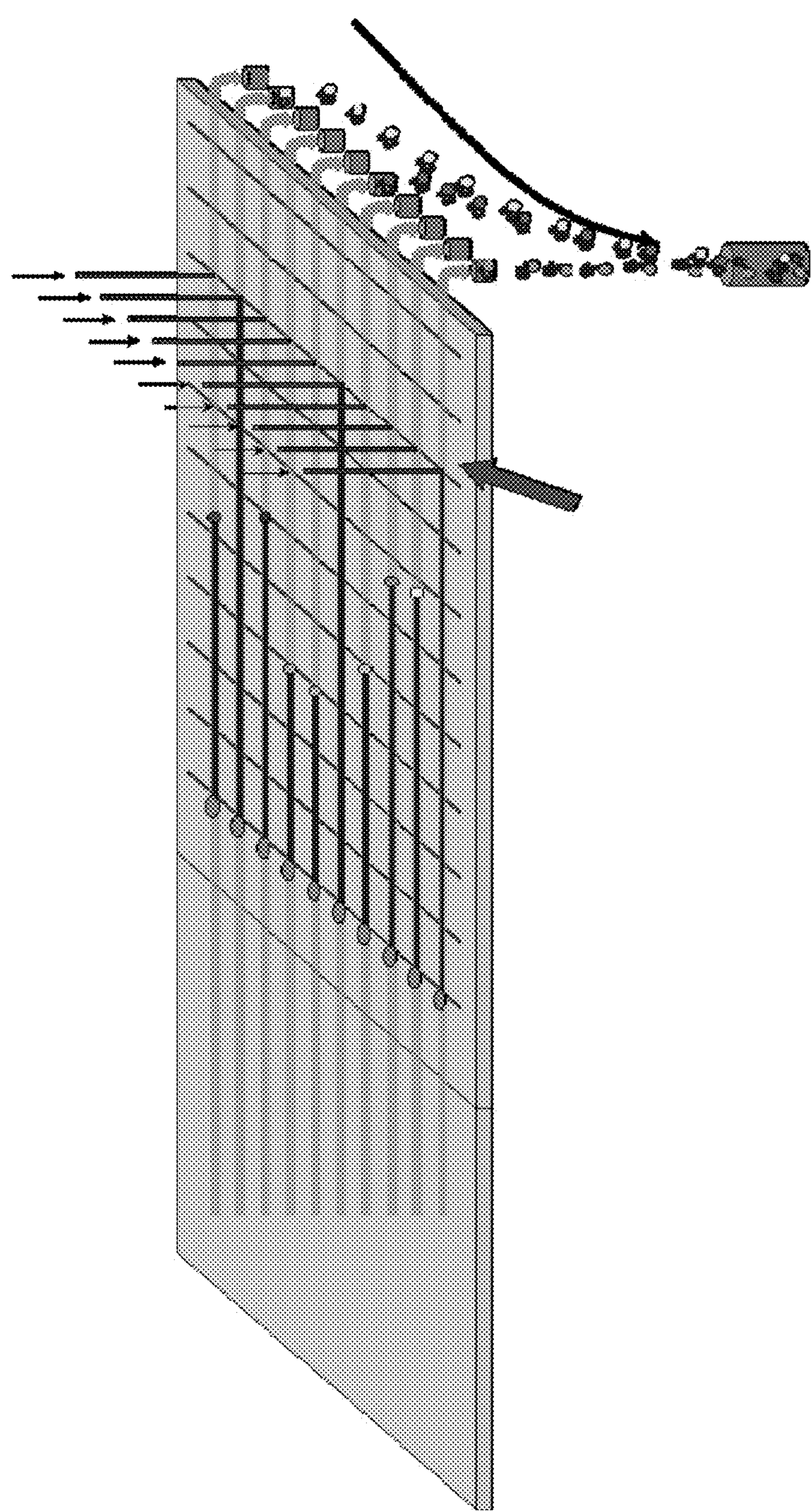
FIG. 14 schematically depicts pooling, amplification and sequencing of the released oligonucleotide fragments). The steps set forth in FIGS. 12-14 are repeated.

The present invention is based in part on the discovery of novel methods and compositions for sequencing large polynucleotides. The methods described herein include one or more of the following steps: obtaining one or more large polynucleotide sequences; cleaving the one or more large polynucleotide sequences into smaller oligonucleotide sequences; immobilizing the oligonucleotide sequences to a support; partially detaching the immobilized oligonucleotide sequences; labelling the non-immobilized ends of the immobilized oligonucleotide sequences; cleaving the labeled, non-immobilized ends of the immobilized oligonucleotide sequences to generate a plurality of labelled oligonucleotide fragments; collecting the labelled oligonucleotide fragments; optionally repeating the labelling, cleaving and collecting steps; and sequencing the labelled oligonucleotide fragments (See FIGS. 1-14).

In certain exemplary embodiments, a polynucleotide (e.g., a nucleic acid sequence of interest) is at least about 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 1,000,000, 2,000,000, 3,000,000, 4,000,000, 5,000,000, 6,000,000, 7,000,000, 8,000,000, 9,000,000, 10,000,000, 15,000,000, 20,000,000, 25,000,000, 30,000,000, 35,000,000, 40,000,000, 45,000,000, 50,000,000 or more nucleic acids in length. In certain aspects, a nucleic acid sequence of interest is a DNA sequence such as, e.g., a regulatory element (e.g., a promoter region, an enhancer region, a coding region, a non-coding region and the like), a gene, a genome, a genomic gap, a DNA sequence involved in a pathway (e.g., a metabolic pathway (e.g., nucleotide metabolism, carbohydrate metabolism, amino acid metabolism, lipid metabolism, co-factor metabolism, vitamin metabolism, energy metabolism and the like), a DNA sequence involved in a signaling pathway, a DNA sequence involved in a biosynthetic pathway, a DNA sequence involved in an immunological pathway, a developmental pathway and the like) and the like. In yet other aspects, a nucleic acid sequence of interest is the length of a gene, e.g., between about 500 nucleotides and 5,000 nucleotides in length. In still other aspects, a nucleic acid sequence of interest is the length of a genome (e.g., a phage genome, a viral genome, a bacterial genome, a fungal genome, a plant genome, an animal genome (e.g., a human genome) or the like).

In certain exemplary embodiments, methods of immobilizing oligonucleotide sequences (e.g., DNA) on a substrate are provided. In certain aspects, an attaching step is performed to such that an oligonucleotide is attached to a trough at the starting line of the substrate. According to one aspect, a single oligonucleotide is attached per trough, which is accomplished by diluting a solution containing the oligonucleotide sequences. In certain aspects, oligonucleotide sequences are prepared by mechanical shearing or cutting (e.g., using one or more sequence-nonspecific or sequence-specific endonucleases) prior to immobilization. Light shearing, mild and/or incomplete cutting can assist in sequence assembly by yielding overlapping sequence reads. Methods and reagents useful for cutting and/or shearing are described further herein.

In certain exemplary embodiments, one or both ends of the sheared oligonucleotide sequences (e.g., sheared polynucleotides (e.g., DNA molecules)) are modified so that they can be bound to a substrate (e.g., at one end of the substrate (e.g., at the starting line of the substrate (See FIG. 1)). The substrate can be simple square grids, checkerboard (e.g., offset) grids, hexagonal arrays and the like. In many embodiments, at least one surface of the solid support will be substantially flat, although in some embodiments it may be desirable to physically separate synthesis regions for different compounds with, for example, wells, raised regions, pins, etched trenches, or the like. Suitable substrates include, but are not limited to, slides, beads, resins, chips, microarrays, particles, strands, semisolid supports, e.g., gels (e.g., agarose, acrylamide, hydrogels, colloids and the like), sheets, tubing, spheres, containers, capillaries, pads, slices, films, culture dishes, plates (e.g., 96-well, 48-well, 24-well, 12-well, eight-well, six-well, four-well, single-well and the like), cell surfaces (e.g., *S. aureus* cells) and the like. In various embodiments, a substrate may be biological, non-biological, organic, inorganic, or any combination thereof.

In certain aspects, sheared or cut oligonucleotide sequences are labeled, at one or both ends, with a moiety that can interact with a binding reagent present at the starting line of the substrate. Any suitable ligand-anti-ligand pair known to those skilled in the art may be used. For example, an oligonucleotide can be labeled with a hapten that is then bound by a capture agent, e.g., as disclosed in Holtke et al., U.S. Pat. Nos. 5,344,757; 5,702,888; and 5,354,657; Huber et al., U.S. Pat. No. 5,198,537; Miyoshi, U.S. Pat. No. 4,849,336; Misiura and Gait, PCT publication WO 91/17160; and the like. Many different hapten-capture agent pairs are available for use with the invention. Exemplary haptens include biotin, des-biotin and other biotin derivatives, dinitrophenol, dansyl, fluorescein, CY5, and other dyes, digoxigenin, DNA binding proteins and the like. For biotin, a capture agent may be avidin, streptavidin, or anti-biotin antibodies. Antibodies may be used as capture agents for the other haptens (dye-antibody pairs are commercially available (Molecular Probes, Eugene, Oreg.)). In certain aspects, oligonucleotide sequences are covalently linked, at one or both ends, to biotin for attachment to a starting line having streptavidin (or another high affinity binding reagent for biotin) bound thereto. In other aspects, oligonucleotide sequences contain, at one or both ends, a sequence specific to one or more DNA binding proteins for attachment to a starting line having antibodies bound thereto that are specific against the one or more the DNA binding proteins.

In other aspects, oligonucleotide sequences contain, at one or both ends, a single-stranded overhang for ligation (or long stable hybridization) to a starting line having complementary single-stranded regions bound thereto. Single-stranded regions can be generated by use of restriction enzymes (after the above ligation) that leave single-stranded overhangs. In still other aspects, oligonucleotide sequences are cleaved by restriction enzymes that leave a single-stranded region, at one or both ends, for ligation to a starting line having sequences homologous to the single-stranded overhangs bound thereto. Longer DNA molecules can be obtained through use of restriction enzymes that cut infrequently or partial cutting by restriction enzymes.

In certain aspects, oligonucleotide sequences are bound, at one or both ends, by proteins that recognize free DNA ends (either single-stranded or double-stranded free ends), for attachment to a starting line having one or more reagents bound thereto that interact with the proteins. In certain aspects, the proteins that recognize free DNA ends are labeled with a hapten (e.g., with biotin or another moiety) for attachment to a starting line having one or more capture agents bound thereto.

In other aspects, oligonucleotide sequences may be attached to a solid support via a linkage moiety. For example, the solid support may be functionalized to provide linkers for covalent attachment to the oligonucleotides. A broad variety of linkage moieties are available in the art of solid phase and microarray oligonucleotide synthesis (see e.g., Pon (1993) *Methods Mol. Biol.* 20:465; Verma et al. (1998) *Ann. Rev. Biochem.* 67:99; U.S. Pat. Nos. 5,739,386, 5,700,642 and 5,830,655; and U.S. Patent Publication Nos. 2003/0186226 and 2004/0106728).

In certain exemplary embodiments, only a single oligonucleotide sequence is attached at a given attachment point of a substrate and only one end of the oligonucleotide sequence (e.g., the 3' or the 5' end) is attached at a given attachment point. This can be achieved using one or any combination of the following: 1) using dilute solutions of oligonucleotide sequences; 2) minimizing the size of each attachment point; 3) flowing an oligonucleotide sequence over the edge of substrate to increase the probability that the two ends of the oligonucleotide sequence are located on opposite sides of the substrate; and 4) using electrophoresis to extend an oligonucleotide prior to binding to a substrate.

As used herein, the terms "attach," "bind" and "immobilize" refer to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in *Molecular Biology of the Cell,* 3d edition, Garland Publishing, 1994.

In certain exemplary embodiments, methods to partially detach oligonucleotide sequences (e.g., DNA (e.g., sheared or cut DNA)) that are attached to a substrate are provided. As used herein, the terms "partially detach" and "partial detach" refer to cleaving an oligonucleotide sequence that is bound to a substrate at two or more locations of the oligonucleotide sequence (e.g., at both its 3' and 5' ends) into two oligonucleotide fragments, each of which is bound to a single, discrete location on the substrate.

Partial detachment can be achieved by exposing oligonucleotide sequences to a cleavage agent that performs one or more of the following functions: endonuclease cleavage, chemical cleavage, laser cleavage, heat cleavage, or any other treatment that will cleave oligonucleotide sequences. Activity of the cleavage agent can be constitutive or conditional. Exposure to the cleavage agent can be achieved using a variety of methods described herein. In certain aspects, troughs containing one or more cleavage agents are provided wherein timing of the cleavage can be controlled by timed release of the partial detaching agent(s), timed release of reagent(s) that will activate one or more partial detaching agents which have been immobilized within the trough (e.g., release of $Mg^{++}$ to activate a restriction enzyme), and/or timed release of components of one or more partial detaching agents that will complement one or more partial, and therefore inactive, partial detaching agents immobilized within the trough.

In other aspects, lines (e.g., raised lines) containing one or more cleavage agents attached thereto (e.g., flexible polymers like polydimethylsiloxane (PDMS) or polymethylmethacrylate (PMMA) used for nanoimprinting (Amsden et al. (2010) *Adv. Mater.* 18; 22(15):1746) and/or DNA-nanostructures (origami) (Douglas et al. (2009) *Nucleic Acids Res.* 37(15): 5001)) are provided, optionally aligned over long (multi-micron) distances (See Church et al., US-2009-0018024, incorporated herein by reference in its entirety for all purposes).

In other aspects, one or more cleavage agents are provided on a physical structure that can then be contacted transiently to nucleic acid sequences (e.g., DNA (e.g., sheared DNA)) that are attached to a substrate, using, e.g., optionally parallel atomic force microscopy (AFM) or related movements with nm-scale feedback.

In still other aspects, cleavage oligonucleotide sequences attached to a substrate is ordered in such a way as to maximize the number and length of oligonucleotide sequences (e.g., DNA molecules) obtained. For example, in certain aspects, cleavage may occur first in the center of the substrate, next in the center of the two flanking halves, and so on.

In certain exemplary embodiments, methods of cleaving immobilized, labelled (optionally partially detached) oligonucleotide sequences to generate labelled oligonucleotide fragments are provided. In certain aspects, cleaving is mediated at a cleavage line (e.g., a snap line) that is parallel to the attachment line. Substrates of the invention will typically include multiple cleavage lines, e.g., 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 or more cleavage lines.

In certain aspects, each oligonucleotide sequence that crosses a cleavage line can be contacted with a cleavage agent to produce a labelled oligonucleotide fragment. As used herein, the term "cleavage agent" refers to a cleaving reagent, a reagent that enables or activates one or more cleaving agents (e.g., release of $Mg^{++}$ to activate a restriction enzyme), a component of a cleaving reagent that will complement a partial, and therefore inactive, cleaving reagent and thus activate the inactive cleaving reagent, and/or agent that terminate cleavage activity. Cleavage agents described herein are useful for cleaving a polynucleotide into a two or more oligonucleotide sequences, for partially detaching one or more oligonucleotide sequences and/or for cleaving oligonucleotide sequences into oligonucleotide fragments.

Cleavage agents include, but are not limited to, sequence-nonspecific nucleases (e.g., such as DNAses, micrococcal nucleases (MNases), Spo11 and the like) and restriction enzymes that produce frequent cuts (e.g., CviI* (Swaminathan et al. (1994) *Nucleic Acids Res.* 22(8):1470)). The REBASE database provides a comprehensive database of information about restriction enzymes, DNA methyltransferases and related proteins involved in restriction-modification. It contains both published and unpublished work with information about restriction endonuclease recognition sites and restriction endonuclease cleavage sites, isoschizomers, commercial availability, crystal and sequence data (see Roberts et al. (2007) *Nucl. Acids Res.* 35:D269 (doi: 10.1093/nar/gk1891)).

Cleavage agents also include chemical cleavage agents (e.g., Cu(II), Ni(II) and Co(III) desferal complexes (Joshi and Ganesh (1992) *Biochem. Biophys. Res. Comm.* 182:588); Cu(II)-thiol complex (Reed and Douglas (1991) *Biochem. J.* 275:601); metalloporphyrins-oxidative cleavage (Meunier (1992) *Chem. Rev.* 92:1411) methidiumpropyl-EDTA-iron (II) (Hertzberg and Dervan (1984) Biochem. 23:3934), and the like), and physical cleavage agents (e.g., laser, heat, blades (e.g., scalpels, razors, knives and the like) and the like). Other useful cleavage agents would be readily apparent to one of ordinary skill in the art.

Timing of cleavage at a cleavage line can be controlled using one or a combination of the following strategies. In certain aspects, directed delivery (e.g., via a capillary or the like) of a cleaving agent is performed. In other aspects, enzymatic, chemical and/or physical methods are used to induce and/or terminate cleaving activity of a cleavage agent. In other aspects, one or more cleavage agents are present on a physical structure that can then be touched transiently to the substrate used to immobilize oligonucleotide sequences, optionally using parallel AFM or related movements with nm-scale feedback.

The extent of cleavage can be controlled using one or a combination of the following strategies. In certain aspects, a cleaving agent is 'sandwiched' by (i.e., proceeded and followed by contact with) solutions that inhibit cleavage (e.g., such as an endonuclease delivered via a capillary). In other aspects, a cleaving reagent or a partial, and therefore inactive, cleaving reagent is immobilized along a cleavage line with directed delivery (e.g., via a capillary or the like) of enabling or activating reagents (e.g., $Mg^{++}$ in the case of restriction enzymes or the complementary components of a cleaving reagent). In yet other aspects, oligonucleotide sequences are maintained in an inhibiting solution (e.g. EDTA, in the case of endonucleases), such that cleavage can only occur at delivery points. Other suitable means of precise delivery (in terms of timing and duration of cleavage activity) would be apparent to one of ordinary skill in the art based on the present disclosure.

Without intending to be bound by scientific theory, oligonucleotide fragments obtained from the first round of cleavage may be too long or otherwise inaccessible for accurate sequencing. Accordingly, in certain aspects, labelled oligonucleotide fragments released after the first round of cleavage will be washed away and not collected.

In certain exemplary embodiments, oligonucleotide sequence labelling (e.g., barcoding) and oligonucleotide fragment collection is carried out in a manner such that the order of fragment release for each original oligonucleotide sequence can be recorded. One or a combination of the following strategies can be used. In certain aspects, unique labels (e.g., barcodes) are used for each reaction, such that no label (e.g., barcode) is used more than once regardless of the trough used or round of labeling. In other aspects, the same label (e.g., barcode) is used in all labellings e.g., in a trough, but each pool is kept separate from all other pools and the order of the pools is recorded. In still other aspects, the same label (e.g., barcode) is used across the entire substrate, but it is changed for each round of labelling. In this case, pooling is useful.

In certain aspects, oligonucleotide fragments are collected into individual containers. In other aspects, oligonucleotide fragments are collected in one or more pools. In yet other aspects, one or more released oligonucleotide fragments can be re-immobilized to a substrate and serve as a new substrate for labelling, cleavage (e.g., at the cleavage line), and collection.

In certain aspects, oligonucleotide fragments are collected into one or more microwells or fluidic flow regions per released oligonucleotide fragment, or pooled with barcodes. A "fluidic flow region" refers to a continuous flow of fluid where various samples are separated from one another by a span of fluid that does not contain one or more of oligonucleotide fragments, gas bubbles, fluid of a different viscosity, and/or fluid that is not miscible with the solution in which the oligonucleotide fragment is suspended.

In certain aspects, oligonucleotide fragments are collected by timing such that one oligonucleotide fragment is expected per microwell or fluidic flow region. In certain aspects, this is performed by physically detecting an oligonucleotide fragment as it passes a collection point. In other aspects, this is performed by timing the collection, i.e., estimating the length of time it would take an oligonucleotide fragment to travel from a point of cleavage to a collection point such that a single oligonucleotide fragment is collected per microwell or fluidic flow region.

In certain exemplary embodiments, the labelling, cleaving, collecting (e.g., pooling and/or amplifying) and/or sequencing steps can be repeated any number of times, e.g., until a portion or all of each immobilized oligonucleotide sequence has been released as labeled oligonucleotide fragments.

In various embodiments, the methods disclosed herein comprise amplification of nucleic acids including, for example, polynucleotides, oligonucleotides and/or oligonucleotide fragments. Amplification may be carried out after each collection step and/or may be carried out one or more times after pooling collected oligonucleotide fragments. Amplification methods may comprise contacting a nucleic acid sequence with one or more primers (e.g., primers that are complementary to barcode sequences) that specifically hybridize to the nucleic acid under conditions that facilitate hybridization and chain extension. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) *Nature Methods* 1:241; and U.S. Pat. Nos. 4,683,195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277:7790), the amplification methods described in U.S. Pat. Nos. 6,391,544, 6,365,375, 6,294,323, 6,261,797, 6,124,090 and 5,612,199, isothermal amplification (e.g., rolling circle amplification (RCA), hyperbranched rolling circle amplification (HRCA), strand displacement amplification (SDA), helicase-dependent amplification (HDA), PWGA or any other nucleic acid amplification method using techniques well known to those of skill in the art.

"Polymerase chain reaction," or "PCR," refers to a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, *PCR: A Practical Approach and PCR2: A Practical Approach* (IRL Press, Oxford, 1991 and 1995, respectively). For example, in a conventional PCR using Taq DNA polymerase, a double stranded target nucleic acid may be denatured at a temperature greater than 90° C., primers annealed at a temperature in the range 50-75° C., and primers extended at a temperature in the range 72-78° C.

The term "PCR" encompasses derivative forms of the reaction, including but not limited to, RT-PCR, real-time PCR, nested PCR, quantitative PCR, multiplexed PCR, assembly PCR and the like. Reaction volumes range from a few hundred nanoliters, e.g., 200 nL, to a few hundred microliters, e.g., 200 microliters. "Reverse transcription PCR," or "RT-PCR," means a PCR that is preceded by a reverse transcription reaction that converts a target RNA to a complementary single stranded DNA, which is then amplified, e.g., Tecott et al., U.S. Pat. No. 5,168,038. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al., U.S. Pat. No. 5,210,015 ("Taqman"); Wittwer et al., U.S. Pat. Nos. 6,174,670 and 6,569,627 (intercalating dyes); Tyagi et al., U.S. Pat. No. 5,925,517 (molecular beacons). Detection chemistries for real-time PCR are reviewed in Mackay et al., *Nucleic Acids Research,* 30:1292-1305 (2002). "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. (1999) *Anal. Biochem.,* 273:221-228 (two-color real-time PCR). Usually, distinct sets of primers are employed for each sequence being amplified. "Quantitative PCR" means a PCR designed to measure the abundance of one or more specific target sequences in a sample or specimen. Techniques for quantitative PCR are well-known to those of ordinary skill in the art, as exemplified in the following references: Freeman et al., *Biotechniques,* 26:112-126 (1999); Becker-Andre et al.,

*Nucleic Acids Research,* 17:9437-9447 (1989); Zimmerman et al., *Biotechniques,* 21:268-279 (1996); Diviacco et al., *Gene,* 122:3013-3020 (1992); Becker-Andre et al., *Nucleic Acids Research,* 17:9437-9446 (1989); and the like.

In certain embodiments, methods of determining the sequence of one or more nucleic acid sequences of interest, e.g., polynucleotides, oligonucleotides and/or oligonucleotide fragments, are provided. Determination of the sequence of a nucleic acid sequence of interest can be performed using variety of sequencing methods known in the art including, but not limited to, sequencing by hybridization (SBH), sequencing by ligation (SBL), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads (U.S. Pat. No. 7,425,431), wobble sequencing (PCT/US05/27695), multiplex sequencing (U.S. Ser. No. 12/027,039, filed Feb. 6, 2008; Porreca et al (2007) *Nat. Methods* 4:931), polymerized colony (POLONY) sequencing (U.S. Pat. Nos. 6,432,360, 6,485,944 and 6,511,803, and PCT/US05/06425); nanogrid rolling circle sequencing (ROLONY) (U.S. Ser. No. 12/120,541, filed May 14, 2008), allele-specific oligo ligation assays (e.g., oligo ligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout) and the like. High-throughput sequencing methods, e.g., on cyclic array sequencing using platforms such as Roche 454, Illumina Solexa, AB-SOLiD, Helicos, Polonator platforms and the like, can also be utilized. High-throughput sequencing methods are described in U.S. Ser. No. 61/162,913, filed Mar. 24, 2009. A variety of light-based sequencing technologies are known in the art (Landegren et al. (1998) *Genome Res.* 8:769-76; Kwok (2000) *Pharmocogenomics* 1:95-100; and Shi (2001) *Clin. Chem.* 47:164-172).

In certain exemplary embodiments, methods of determining the sequence of one or more nucleic acid sequences of interest, e.g., polynucleotides, oligonucleotides and/or oligonucleotide fragments, are provided that utilize nested deletions. In certain aspects, labelled oligonucleotide fragments are collected, circularized and amplified. A series of sequentially related deletion-bearing derivatives can then be performed such that sequencing from the label (e.g., one or more barcode sequences) of the derivatives will yield a set of sequences that can then be ordered to give the sequence of the original fragment. This strategy is particularly useful when one wants to apply short-read (e.g., less than 100 bp) sequencing methods to DNA fragments that are greater than 100 bp.

Embodiments of the present invention are directed to oligonucleotide sequences having one or two or more labels (e.g., barcode sequences) attached thereto. As used herein, the term "barcode" refers to a unique oligonucleotide sequence that allows a corresponding nucleic acid sequence (e.g., an oligonucleotide fragment) to be identified, retrieved and/or amplified. In certain embodiments, barcodes can each have a length within a range of from 4 to 36 nucleotides, or from 6 to 30 nucleotides, or from 8 to 20 nucleotides. In certain exemplary embodiments, a barcode has a length of 4 nucleotides. In certain aspects, the melting temperatures of barcodes within a set are within 10° C. of one another, within 5° C. of one another, or within 2° C. of one another. In other aspects, barcodes are members of a minimally cross-hybridizing set. That is, the nucleotide sequence of each member of such a set is sufficiently different from that of every other member of the set that no member can form a stable duplex with the complement of any other member under stringent hybridization conditions. In one aspect, the nucleotide sequence of each member of a minimally cross-hybridizing set differs from those of every other member by at least two nucleotides. Barcode technologies are known in the art and are described in Winzeler et al. (1999) *Science* 285:901; Brenner (2000) *Genome Biol.* 1:1 Kumar et al. (2001) *Nature Rev.* 2:302; Giaever et al. (2004) *Proc. Natl. Acad. Sci. USA* 101:793; Eason et al. (2004) *Proc. Natl. Acad. Sci. USA* 101:11046; and Brenner (2004) *Genome Biol.* 5:240.

In certain aspects, a label is a fluorescent label that is directly or indirectly attached to an oligonucleotide sequence. Fluorescent labels and their attachment to oligonucleotides are described in many reviews, including Haugland, *Handbook of Fluorescent Probes and Research Chemicals*, Ninth Edition (Molecular Probes, Inc., Eugene, 2002); Keller and Manak, DNA Probes, 2nd Edition (Stockton Press, New York, 1993); Eckstein, editor, *Oligonucleotides and Analogues: A Practical Approach* (IRL Press, Oxford, 1991); Wetmur, *Critical Reviews in Biochemistry and Molecular Biology,* 26:227-259 (1991); and the like. Particular methodologies applicable to the invention are disclosed in the following sample of references: Fung et al., U.S. Pat. No. 4,757,141; Hobbs, Jr., et al. U.S. Pat. No. 5,151,507; Cruickshank, U.S. Pat. No. 5,091,519. In one aspect, one or more fluorescent dyes are used as labels for labeled target sequences, e.g., as disclosed by Menchen et al., U.S. Pat. No. 5,188,934 (4,7-dichlorofluorscein dyes); Begot et al., U.S. Pat. No. 5,366,860 (spectrally resolvable rhodamine dyes); Lee et al., U.S. Pat. No. 5,847,162 (4,7-dichlororhodamine dyes); Khanna et al., U.S. Pat. No. 4,318,846 (ether-substituted fluorescein dyes); Lee et al., U.S. Pat. No. 5,800,996 (energy transfer dyes); Lee et al., U.S. Pat. No. 5,066,580 (xanthine dyes): Mathies et al., U.S. Pat. No. 5,688,648 (energy transfer dyes); and the like. Labelling can also be carried out with quantum dots, as disclosed in the following patents and patent publications: U.S. Pat. Nos. 6,322,901; 6,576,291; 6,423,551; 6,251,303; 6,319,426; 6,426,513; 6,444,143; 5,990,479; 6,207,392; 2002/0045045; 2003/0017264; and the like. As used herein, the term "fluorescent label" includes a signaling moiety that conveys information through the fluorescent absorption and/or emission properties of one or more molecules. Such fluorescent properties include fluorescence intensity, fluorescence life time, emission spectrum characteristics, energy transfer, and the like.

Terms and symbols of nucleic acid chemistry, biochemistry, genetics, and molecular biology used herein follow those of standard treatises and texts in the field, e.g., Komberg and Baker, *DNA Replication*, Second Edition (W.H. Freeman, New York, 1992); Lehninger, *Biochemistry*, Second Edition (Worth Publishers, New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

"Complementary" or "substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See Kanehisa (1984) *Nucl. Acids Res.* 12:203.

"Complex" refers to an assemblage or aggregate of molecules in direct or indirect contact with one another. In one aspect, "contact," or more particularly, "direct contact," in reference to a complex of molecules or in reference to specificity or specific binding, means two or more molecules are close enough so that attractive noncovalent interactions, such as van der Waal forces, hydrogen bonding, ionic and hydrophobic interactions, and the like, dominate the interaction of the molecules. In such an aspect, a complex of molecules is stable in that under assay conditions the complex is thermodynamically more favorable than a non-aggregated, or non-complexed, state of its component molecules. As used herein, "complex" refers to a duplex or triplex of polynucleotides or a stable aggregate of two or more proteins. In regard to the latter, a complex is formed by an antibody specifically binding to its corresponding antigen.

"Duplex" refers to at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. In one aspect, stable duplex means that a duplex structure is not destroyed by a stringent wash, e.g., conditions including temperature of about 5° C. less that the $T_m$ of a strand of the duplex and low monovalent salt concentration, e.g., less than 0.2 M, or less than 0.1 M. "Perfectly matched" in reference to a duplex means that the polynucleotide or oligonucleotide strands making up the duplex form a double stranded structure with one another such that every nucleotide in each strand undergoes Watson-Crick base pairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Genetic locus," or "locus" refers to a contiguous subregion or segment of a genome. As used herein, genetic locus, or locus, may refer to the position of a nucleotide, a gene, or a portion of a gene in a genome, including mitochondrial DNA, or it may refer to any contiguous portion of genomic sequence whether or not it is within, or associated with, a gene. In one aspect, a genetic locus refers to any portion of genomic sequence, including mitochondrial DNA, from a single nucleotide to a segment of few hundred nucleotides, e.g. 100-300, in length. Usually, a particular genetic locus may be identified by its nucleotide sequence, or the nucleotide sequence, or sequences, of one or both adjacent or flanking regions. In another aspect, a genetic locus refers to the expressed nucleic acid product of a gene, such as an RNA molecule or a cDNA copy thereof.

"Hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, i.e., conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, *Molecular Cloning A Laboratory Manual,* 2nd Ed. Cold Spring Harbor Press (1989) and Anderson *Nucleic Acid Hybridization,* 1st Ed., BIOS Scientific Publishers Limited (1999). "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

"Kit" refers to any delivery system for delivering materials or reagents for carrying out a method of the invention. In the context of assays, such delivery systems include systems that allow for the storage, transport, or delivery of reaction reagents (e.g., primers, enzymes, microarrays, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials for assays of the invention. Such contents may be delivered to the intended recipient together or separately. For example, a first container may contain an enzyme for use in an assay, while a second container contains primers.

"Ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references: Whitely et al., U.S. Pat. No. 4,883,750; Letsinger et al., U.S. Pat. No. 5,476,930; Fung et al., U.S. Pat. No. 5,593,826; Kool, U.S. Pat. No. 5,426,180; Landegren et al., U.S. Pat. No. 5,871,921; Xu and Kool (1999) *Nucl. Acids Res.* 27:875; Higgins et al., *Meth. in Enzymol*. (1979) 68:50; Engler et al. (1982) *The Enzymes,* 15:3 (1982); and Namsaraev, U.S. Patent Pub. 2004/0110213.

"Amplifying" includes the production of copies of a nucleic acid molecule of the array or a nucleic acid molecule bound to a bead via repeated rounds of primed enzymatic synthesis. "In situ" amplification indicated that the amplification takes place with the template nucleic acid molecule positioned on a support or a bead, rather than in solution. In situ amplification methods are described in U.S. Pat. No. 6,432,360.

"Support" can refer to a matrix upon which nucleic acid molecules of a nucleic acid array are placed. The support can be solid or semi-solid or a gel. "Semi-solid" refers to a compressible matrix with both a solid and a liquid component, wherein the liquid occupies pores, spaces or other interstices between the solid matrix elements. Semi-solid supports can be selected from polyacrylamide, cellulose, polyamide (nylon) and crossed linked agarose, dextran and polyethylene glycol.

"Randomly-patterned" or "random" refers to non-ordered, non-Cartesian distribution (in other words, not arranged at pre-determined points along the x- or y-axes of a grid or at defined "clock positions," degrees or radii from the center of a radial pattern) of nucleic acid molecules over a support, that is not achieved through an intentional design (or program by which such design may be achieved) or by placement of individual nucleic acid features. Such a "randomly-patterned" or "random" array of nucleic acids may be achieved by dropping, spraying, plating or spreading a solution, emulsion, aerosol, vapor or dry preparation comprising a pool of nucleic acid molecules onto a support and allowing the nucleic acid molecules to settle onto the support without intervention in any manner to direct them to specific sites thereon. Arrays of the invention can be randomly patterned or random.

"Heterogeneous" refers to a population or collection of nucleic acid molecules that comprises a plurality of different sequences. According to one aspect, a heterogeneous pool of oligonucleotide sequences is provided with an article of manufacture (e.g., a microarray).

"Nucleoside" as used herein includes the natural nucleosides, including 2'-deoxy and 2'-hydroxyl forms, e.g. as described in Komberg and Baker, *DNA Replication,* 2nd Ed. (Freeman, San Francisco, 1992). "Analogs" in reference to nucleosides includes synthetic nucleosides having modified base moieties and/or modified sugar moieties, e.g., described by Scheit, *Nucleotide Analogs* (John Wiley, New York, 1980); Uhlman and Peyman, *Chemical Reviews,* 90:543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al., *Exp. Opin. Ther. Patents,* 6: 855-870 (1996); Mesmaeker et al., *Current Opinion in Structural Biology,* 5:343-355 (1995); and the like. Exemplary types of polynucleotides that are capable of enhancing duplex stability include oligonucleotide phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids (LNAs), and like compounds. Such oligonucleotides are either available commercially or may be synthesized using methods described in the literature.

As used herein, the terms "nucleic acid molecule," "nucleic acid sequence," "nucleic acid fragment," "oligonucleotide," "oligonucleotide fragment" and "polynucleotide" are used interchangeably and are intended to include, but are not limited to, a polymeric form of nucleotides that may have various lengths, either deoxyribonucleotides or ribonucleotides, or analogs thereof. Nucleic acid molecules include single stranded DNA (ssDNA), double stranded DNA (dsDNA), single stranded RNA (ssRNA) and double stranded RNA (dsRNA). Different nucleic acid molecules may have different three-dimensional structures, and may perform various functions, known or unknown. Non-limiting examples of nucleic acid molecules include a gene, a gene fragment, a genomic gap, an exon, an intron, intergenic DNA (including, without limitation, heterochromatic DNA), messenger RNA (mRNA), transfer RNA, ribosomal RNA, ribozymes, small interfering RNA (siRNA), miRNA, small nucleolar RNA (snoRNA), cDNA, recombinant polynucleotides, branched polynucleotides, plasmids, vectors, isolated DNA of a sequence, isolated RNA of a sequence, nucleic acid probes, and primers. Nucleic acid molecules useful in the methods described herein may comprise natural nucleic acid sequences and variants thereof, artificial nucleic acid sequences, or a combination of such sequences.

An oligonucleotide sequence refers to a linear polymer of natural or modified nucleosidic monomers linked by phosphodiester bonds or analogs thereof. The term "oligonucleotide" usually refers to a shorter polymer, e.g., comprising from about 3 to about 100 monomers, and the term "polynucleotide" usually refers to longer polymers, e.g., comprising from about 100 monomers to many thousands of monomers, e.g., 10,000 monomers, or more An "oligonucleotide fragment" refers to an oligonucleotide sequence that has been cleaved into two or more smaller oligonucleotide sequences. Oligonucleotides comprising probes or primers usually have lengths in the range of from 12 to 60 nucleotides, and more usually, from 18 to 40 nucleotides. Oligonucleotides and polynucleotides may be natural or synthetic. Oligonucleotides and polynucleotides include deoxyribonucleosides, ribonucleosides, and non-natural analogs thereof, such as anomeric forms thereof, peptide nucleic acids (PNAs), and the like, provided that they are capable of specifically binding to a target genome by way of a regular pattern of monomer-to-monomer interactions, such as Watson-Crick type of base pairing, base stacking, Hoogsteen or reverse Hoogsteen types of base pairing, or the like.

Usually nucleosidic monomers are linked by phosphodiester bonds. Whenever an oligonucleotide is represented by a sequence of letters, such as "ATGCCTG," it will be understood that the nucleotides are in 5' to 3' order from left to right and that "A" denotes deoxyadenosine, "C" denotes deoxycytidine, "G" denotes deoxyguanosine, "T" denotes deoxythymidine, and "U" denotes the ribonucleoside, uridine, unless otherwise noted. Usually oligonucleotides comprise the four natural deoxynucleotides; however, they may also comprise ribonucleosides or non-natural nucleotide analogs. It is clear to those skilled in the art when oligonucleotides having natural or non-natural nucleotides may be employed in methods and processes described herein. For example, where processing by an enzyme is called for, usually oligonucleotides consisting solely of natural nucleotides are required. Likewise, where an enzyme has specific oligonucleotide or polynucleotide substrate requirements for activity, e.g., single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al., *Molecular Cloning*, Second Edition (Cold Spring Harbor Laboratory, New York, 1989), and like references. Oligonucleotides and polynucleotides may be single stranded or double stranded.

Nucleic acid molecules may optionally include one or more non-standard nucleotide(s), nucleotide analog(s) and/or modified nucleotides. Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

In certain exemplary embodiments, large polynucleotides are provided. In certain aspects, isolation techniques that maximize the lengths of polynucleotides (e.g., DNA molecules) obtained are used. For example, in situ lysis or deproteinization (e.g., with EDTA, detergent, protease, any combinations thereof and the like) after agarose embedding (as routinely performed for pulsed field gel electrophoresis) can be used to obtain polynucleotides.

Nucleic acid molecules may be isolated from natural sources or purchased from commercial sources. Oligonucleotide sequences may also be prepared by any suitable method, e.g., standard phosphoramidite methods such as those described by Beaucage and Carruthers ((1981) *Tetrahedron Lett.* 22: 1859) or the triester method according to Matteucci et al. (1981) *J. Am. Chem. Soc.* 103:3185), or by other chemical methods using either a commercial automated oligonucleotide synthesizer or high-throughput, high-density array methods known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

Nucleic acid molecules may be obtained from one or more biological samples. As used herein, a "biological sample" may be a single cell or many cells. A biological sample may comprise a single cell type or a combination of two or more cell types. A biological sample further includes a collection of cells that perform a similar function such as those found, for example, in a tissue. Accordingly, certain aspects of the invention are directed to biological samples containing one or more tissues. As used herein, a tissue includes, but is not limited to, epithelial tissue (e.g., skin, the lining of glands, bowel, skin and organs such as the liver, lung, kidney), endothelium (e.g., the lining of blood and lymphatic vessels), mesothelium (e.g., the lining of pleural, peritoneal and pericardial spaces), mesenchyme (e.g., cells filling the spaces between the organs, including fat, muscle, bone, cartilage and tendon cells), blood cells (e.g., red and white blood cells), neurons, germ cells (e.g., spermatozoa, oocytes), amniotic fluid cells, placenta, stem cells and the like. A tissue sample includes microscopic samples as well as macroscopic samples.

In certain aspects, nucleic acid sequences derived or obtained from one or more organisms are provided. As used herein, the term "organism" includes, but is not limited to, a human, a non-human primate, a cow, a horse, a sheep, a goat, a pig, a dog, a cat, a rabbit, a mouse, a rat, a gerbil, a frog, a toad, a fish (e.g., *Danio rerio*) a roundworm (e.g., *C. elegans*) and any transgenic species thereof. The term "organism" further includes, but is not limited to, a yeast (e.g., *S. cerevisiae*) cell, a yeast tetrad, a yeast colony, a bacterium, a bacterial colony, a virion, virosome, virus-like particle and/or cultures thereof, and the like.

Isolation, extraction or derivation of nucleic acid sequences may be carried out by any suitable method. Isolating nucleic acid sequences from a biological sample generally includes treating a biological sample in such a manner that nucleic acid sequences present in the sample are extracted and made available for analysis. Any isolation method that results in extracted nucleic acid sequences may be used in the practice of the present invention. It will be understood that the particular method used to extract nucleic acid sequences will depend on the nature of the source.

Methods of DNA extraction are well-known in the art. A classical DNA isolation protocol is based on extraction using organic solvents such as a mixture of phenol and chloroform, followed by precipitation with ethanol (J. Sambrook et al., "Molecular Cloning: A Laboratory Manual," 1989, 2nd Ed., Cold Spring Harbour Laboratory Press: New York, N.Y.). Other methods include: salting out DNA extraction (P. Sunnucks et al., Genetics, 1996, 144: 747-756; S. M. Aljanabi and I. Martinez, Nucl. Acids Res. 1997, 25: 4692-4693), trimethylammonium bromide salts DNA extraction (S. Gustincich et al., BioTechniques, 1991, 11: 298-302) and guanidinium thiocyanate DNA extraction (J. B. W. Hammond et al., Biochemistry, 1996, 240: 298-300). A variety of kits are commercially available for extracting DNA from biological samples (e.g., BD Biosciences Clontech (Palo Alto, Calif.): Epicentre Technologies (Madison, Wis.); Gentra Systems, Inc. (Minneapolis, Minn.); MicroProbe Corp. (Bothell, Wash.); Organon Teknika (Durham, N.C.); and Qiagen Inc. (Valencia, Calif.)).

Methods of RNA extraction are also well known in the art (see, for example, J. Sambrook et al., "Molecular Cloning: A Laboratory Manual" 1989, 2nd Ed., Cold Spring Harbour Laboratory Press: New York) and several kits for RNA extraction from bodily fluids are commercially available (e.g., Ambion, Inc. (Austin, Tex.); Amersham Biosciences (Piscataway, N.J.); BD Biosciences Clontech (Palo Alto, Calif.); BioRad Laboratories (Hercules, Calif.); Dynal Biotech Inc. (Lake Success, N.Y.); Epicentre Technologies (Madison, Wis.); Gentra Systems, Inc. (Minneapolis, Minn.); GIBCO BRL (Gaithersburg, Md.); Invitrogen Life Technologies (Carlsbad, Calif.); MicroProbe Corp. (Bothell, Wash.); Organon Teknika (Durham, N.C.); Promega, Inc. (Madison, Wis.); and Qiagen Inc. (Valencia, Calif.)).

"Polymorphism" or "genetic variant" means a substitution, inversion, insertion, or deletion of one or more nucleotides at a genetic locus, or a translocation of DNA from one genetic locus to another genetic locus. In one aspect, polymorphism means one of multiple alternative nucleotide sequences that may be present at a genetic locus of an individual and that may comprise a nucleotide substitution, insertion, or deletion with respect to other sequences at the same locus in the same individual, or other individuals within a population. An individual may be homozygous or heterozygous at a genetic locus; that is, an individual may have the same nucleotide sequence in both alleles, or have a different nucleotide sequence in each allele, respectively. In one aspect, insertions or deletions at a genetic locus comprises the addition or the absence of from 1 to 10 nucleotides at such locus, in comparison with the same locus in another individual of a population (or another allele in the same individual). Usually, insertions or deletions are with respect to a major allele at a locus within a population, e.g., an allele present in a population at a frequency of fifty percent or greater.

"Primer" includes an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of between 3 to 36 nucleotides, also 5 to 24 nucleotides, also from 14 to 36 nucleotides. Primers within the scope of the invention include orthogonal primers, amplification primers, constructions primers and the like. Pairs of primers can flank a sequence of interest or a set of sequences of interest. Primers and probes can be degenerate in sequence. Primers within the scope of the present invention bind adjacent to a target sequence (e.g., an oligonucleotide fragment, a barcode sequence or the like).

"Specific" or "specificity" in reference to the binding of one molecule to another molecule, such as an amplification or sequencing primer to a barcode sequence, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. In certain aspects, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak non-covalent chemical interactions, such as van der Waal forces, hydrogen bonding, base-stacking interactions, ionic and hydrophobic interactions, and the like, dominate the interaction of the molecules.

"Spectrally resolvable" in reference to a plurality of fluorescent labels means that the fluorescent emission bands of the labels are sufficiently distinct, i.e., sufficiently non-overlapping, that molecular tags to which the respective labels are attached can be distinguished on the basis of the fluorescent signal generated by the respective labels by standard photodetection systems, e.g., employing a system of band pass filters and photomultiplier tubes, or the like, as exemplified by the systems described in U.S. Pat. Nos. 4,230,558; 4,811,218, or the like, or in Wheeless et al., pgs. 21-76, in *Flow Cytometry: Instrumentation and Data Analysis* (Academic Press, New York, 1985). In one aspect, spectrally resolvable organic dyes, such as fluorescein, rhodamine, and the like, means that wavelength emission maxima are spaced at least 20 nm apart, and in another aspect, at least 40 nm apart. In another aspect, chelated lanthanide compounds, quantum dots, and the like, spectrally resolvable means that wavelength emission maxima are spaced at least 10 nm apart, and in a further aspect, at least 15 nm apart.

"$T_m$" is used in reference to "melting temperature." Melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation. $T_m$=81.5+0.41 (% G+C), when a nucleic acid is in aqueous solution at 1 M NaCl (see e.g., Anderson and Young, "Quantitative Filter Hybridization," in *Nucleic Acid Hybridization* (1985). Other references (e.g., Allawi, H. T. & Santa Lucia, J., Jr., *Biochemistry* 36, 10581-94 (1997)) include alternative methods of computation which take structural and environmental, as well as sequence characteristics into account for the calculation of $T_m$.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures and accompanying claims.

Example I

Stretching and Attaching Nucleic Acid Molecules to a Substrate

The cell cultures are grown at 37° C. The cultures are rinsed with room temperature Dulbecco's phosphate-buffered saline (DPBS), and the cells are lifted with either Accutase or trypsin. Following centrifugation, the cells are resuspended at $3\times10^7$ cells per ml in DPBS. Equal volumes of method 1% InCert agarose (Lonza Rockland, Inc., Rockland, Me.) in DPBS are added to the cells at 42° C. The cell solution is pipetted into a chilled plastic mold with 0.5- by 0.2-cm wells with a depth of 0.9 cm for preparing DNA gel plugs. The gel plugs are allowed to polymerize on ice for 30 minutes and ware then be pushed out of the plastic mold into a 50-ml centrifuge tube containing lysis buffer (1% n-lauroylsarcosine (Sigma-Aldrich, St. Louis, Mo.), 0.5 M EDTA [pH 8], and 20 mg/ml proteinase K). The gel plugs remain at 50° C. for 64 hours and are treated with 30 mg/ml proteinase K, recombinant PCR grade (Roche Diagnostics, Mannheim, Germany), every 24 hours.

Enzymatic Digestion of Genomic DNA

The gel plugs are rinsed several times with Tris-EDTA (TE) and once with phenylmethanesulfonyl fluoride (Sigma-Aldrich, St. Louis, Mo.). The plugs are rinsed with 10 mM $MgCl_2$ and 10 mM Tris-HCl (pH 8.0). The genomic DNA in the gel plugs is digested with 50 units of PmeI (New England Biolabs Inc., Ipswich, Mass.) per plug in approximately 150 μl of digestion buffer containing 2×BSA (New England Biolabs Inc., Ipswich, Mass.) and 40 μM spermidine (New England Biolabs, Ipswich, Mass.) at 37° C. overnight.

Pulsed-Filed Gel Electrophoresis (PFGE)

The digested gel plugs are rinsed with TE and cast into a 0.7% gel (SeaPlaque GTG agarose (Lonza Rockland, Inc., Rockland, Me.)). A gel lambda ladder PFG marker and yeast chromosome PFG marker (both from New England Biolabs, Ipswich, Mass.) are cast next to the gel plugs.

Southern Transfer and Hybridization

A Southern transfer is performed to determine the location for the DNA fragment on the gel. The region of the gel containing the segment of interest is excised and set aside, while the rest of the DNA (which includes the chromosome ladders) is transferred to a membrane (Hybond-XL (Amersham Biosciences, Piscataway, N.J.)) and hybridized with probes. Radiography is used to determine the location of the appropriate DNA segment or locus from the gel transfer. The remainder of the saved DNA gel slice is then cut into sequential 0.5-mm pieces of DNA and stored at 4° C. in 50 mM EDTA and 10 mM Tris-HCl (pH 8.0).

Stretching the DNA Molecules

The DNA molecules are stretched and fixed on glass slides and then hybridized with biotinylated probes that specify sequences on the molecule. Samples of gel slices from the appropriate positions in the pulsed-field electrophoresis gel are separately melted, and aliquots of the resulting DNA solutions are separately stretched on microscope slides. The gel section containing the segment of interest is sliced into 1-mm sections, rinsed with TE several times, and melted at 72° C. for 15 min. GELase enzyme (1 unit per 50 μl of agarose suspension) (Epicentre Biotechnologies, Madison, Wis.) is carefully added to digest the agarose. The DNA remains at 45° C. for a minimum of 2 hours, and the DNA strands are incubated with YOYO-1 iodide (Molecular Probes, Eugene, Oreg.) for at least 1 hour prior to stretching on 3-aminopropyltriethoxysilane (Sigma-Aldrich, St. Louis, Mo.)-coated glass slides. The DNA is pipetted along one side of a coverslip that is placed on top of a silane-treated glass slide and allowed to enter by capillary action. The DNA is denatured with sodium hydroxide in ethanol and then fixed with glutaraldehyde.

REFERENCE

Schultz et al. (2010) *Mol. Cell. Biol.* 30(18):4521, incorporated herein by reference in its entirety for all purposes.

Example II

Collect DNA, Pool, Amplify and Sequence

Oligonucleotide fragments are collected (e.g., into tubes, microwells, fluidic flow regions or the like). In certain aspects, each oligonucleotide fragment is collected separately and, optionally, pooled. In other aspects, oligonucleotide fragments from each snap line are collected and pooled. In yet other aspects, oligonucleotide fragments along a substrate trough are collected and pooled. In still other aspects, substantially all oligonucleotide fragments from the substrate are collected and pooled.

The collected oligonucleotide fragments are then amplified using any of a variety of methods known to those of skill in the art, including, but not limited to, PCR, RCA (e.g., linear or hyperbranched amplification) or other isothermal or thermal-cycling methods. In certain aspects, the collected oligonucleotide fragments are sequenced without further manipulations to generate short oligonucleotide fragment reads. In other aspects, oligonucleotide fragments are circularized and then sequenced. Circularization is achieved using any of a variety of methods known to those of ordinary skill in the art such as, e.g., restriction digestion/circularization, shearing/circularization and the like. In other aspects, oligonucleotide sequences are concatamerized and then sequenced.

In certain aspects, collected oligonucleotide fragments have barcode labels at one end, i.e., the order is 5' (first) common primer sequence, then unique variable (barcode) sequence that corresponds to substrate trough number and/or and snap-line number, and then the DNA fragment (e.g., genome fragment) of interest. Each such oligonucleotide fragment is then either ligated at the other end to a second common primer sequence (optionally with a panhandle overhang) as in ligation-mediated PCR, or used in concatamer-mediated multiple displacement amplification (see protocol details in Shoaib et al. (2008) *BMC Genomics* 9:415, doi: 10.1186/1471-2164-9-415). Performing PCR at the end of the procedure typically gives asymmetrically labeled linear double stranded DNA, which can be made selectively single-stranded for sequencing from the first common primer region and optionally then the second common primer.

In certain aspects, long oligonucleotide fragments are used to make a series of nested deletions. Such a protocol is particularly useful when long oligonucleotide fragments are being used, as it allows one the ability to sequentially determine the nucleic acid sequences of portions of the oligonucleotide fragment that would otherwise be too distant from a primer site to be successfully sequenced. In other aspects, long oligonucleotide fragments are treated as new substrates for binding and sub-sequence snapping.

After amplification, sequencing is performed to obtain oligonucleotide fragment reads. Sequencing is carried out using any method appropriate for the length of the oligonucleotide fragments. In certain aspects, next generation or high-throughput sequencing with long reads or paired end reads is used. High-throughput sequencing methods include, e.g., platforms such as Illumina flow cell, ABI, Complete Genomics' Nano Bowl, Roche 454, Illumina Solexa, AB-SOLiD, Helicos, Polonator platforms and the like.

In certain exemplary embodiments, sequencing is performed from common primer sequences, through the barcode and into the unknown region using either sequencing by polymerase with reversible terminators (for example, Illumina reads of 100 bp or 454 reads of 800 bp) or sequencing by cyclic ligation (ABI-SOLiD, 70 bp reads). Only reads with unambiguous barcodes and high overall quality are retained. Assembly software uses the barcodes to determine order in final sequences. In other aspects, sequencing is performed from one or more barcode regions.

After the sequencing step, the oligonucleotide reads are assembled. The assembled oligonucleotide reads correspond to all or a portion of a nucleic acid sequence of interest (e.g., a genomic DNA sequence of interest). In certain aspects, assembly is performed de novo, e.g., by using overlapping regions of oligonucleotide reads to determine the order of the sequencing reads relative to one another. De novo sequencing is useful for determining unknown sequences, e.g., heterochromatin sequences. In other aspects, an existing backbone sequence is used as scaffold to assemble an oligonucleotide that is similar but not necessarily identical to the backbone sequence. In certain aspects, long oligonucleotide reads corresponding to oligonucleotide fragments from various troughs and from both orientations of the long oligonucleotide fragments can be aligned using sequences unique in the genome and the distances known from the order and position of snapping. In certain aspects, alignment software is used to aid in assembly and/or determining the sequence of the assembled oligonucleotide reads.

What is claimed is:

1. A method for determining the nucleic acid sequence of a polynucleotide that is at least 1500 nucleotides in length comprising the steps of:

a) providing a polynucleotide;

b) cleaving the polynucleotide into a plurality of oligonucleotide sequences;

c) immobilizing only one end of each of the plurality of oligonucleotide sequences to a given attachment point on a first end of a substrate;

d) arranging the plurality of oligonucleotide sequences substantially linearly on the substrate;

e) attaching a label to a non-immobilized end of each of the plurality of oligonucleotide sequences;

f) cleaving the plurality of oligonucleotide sequences at a cleavage line substantially perpendicular to said plurality of oligonucleotide sequences to generate a plurality of labelled oligonucleotide fragments;

g) collecting the plurality of oligonucleotide fragments;

h) sequencing the plurality of oligonucleotide fragments to obtain oligonucleotide reads;

i) assembling the oligonucleotide reads; and h) determining the nucleic acid sequence of the assembled oligonucleotide reads to determine the nucleic acid sequence of the polynucleotide.

2. The method of claim 1, wherein steps e)-g) are repeated.

3. The method of claim 2, wherein the plurality of oligonucleotide fragments obtained from each repeat of step g) are pooled.

4. The method of claim 2, wherein the plurality of oligonucleotide fragments obtained from each repeat of step g) are kept separate from one another.

5. The method of claim 1, further including the step of amplifying the collected oligonucleotide fragments.

6. The method of claim 5, wherein the step of amplifying is performed using a method selected from the group consisting of PCR, linear rolling circle amplification (RCA) and hyperbranched RCA.

7. The method of claim 1, wherein the polynucleotide is at least 2000 base pairs in length.

8. The method of claim 1, wherein the polynucleotide is at least 5000 base pairs in length.

9. The method of claim 1, wherein the polynucleotide is between 5000 base pairs and 34,000 base pairs in length.

10. The method of claim 1, wherein the polynucleotide is DNA.

11. The method of claim 1, wherein the polynucleotide is a portion of a genome.

12. The method of claim 11, wherein the portion of the genome comprises one or more genomic gaps.

13. The method of claim 1, further comprising partially detaching the plurality of oligonucleotide sequences of step c).

14. The method of claim 1, wherein the label is a barcode sequence.

15. A method for determining the nucleic acid sequence of a polynucleotide that is at least 1500 nucleotides in length comprising the steps of:

a) providing a polynucleotide;

b) cleaving the polynucleotide into a plurality of oligonucleotide sequences;

c) immobilizing only one end of each of the plurality of oligonucleotide sequences to a given attachment point on a first end of a substrate;

d) partially detaching the plurality of oligonucleotide sequences;

e) arranging the plurality of oligonucleotide sequences substantially linearly on the substrate;

f) attaching a label to a non-immobilized end of each of the plurality of oligonucleotide sequences;

g) cleaving the plurality of oligonucleotide sequences at a cleavage line substantially perpendicular to said plurality of oligonucleotide sequences to generate a plurality of labelled oligonucleotide fragments;

h) collecting the plurality of oligonucleotide fragments;

i) sequencing the plurality of oligonucleotide fragments to obtain oligonucleotide reads;

j) assembling the oligonucleotide reads; and k) determining the nucleic acid sequence of the assembled oligonucleotide reads to determine the nucleic acid sequence of the polynucleotide.

16. The method of claim 15, wherein the partially detaching step is performed by contacting one or more of the plurality of oligonucleotide sequences with one or any combination of an endonuclease, a chemical, light, heat and a blade.

17. A method for determining the nucleic acid sequence of a polynucleotide that is at least 1500 nucleotides in length comprising the steps of:

a) providing a polynucleotide;

b) cleaving the polynucleotide into a plurality of oligonucleotide sequences;

c) immobilizing only one end of each of the plurality of oligonucleotide sequences to a given attachment point on a first end of a substrate;

d) arranging the plurality of oligonucleotide sequences substantially linearly on the substrate;

e) attaching a barcode sequence to a non-immobilized end of each of the plurality of oligonucleotide sequences;

f) cleaving the plurality of oligonucleotide sequences at a cleavage line substantially perpendicular to said plurality of oligonucleotide sequences to generate a plurality of labelled oligonucleotide fragments;

g) collecting the plurality of oligonucleotide fragments;

h) repeating steps e)-g); and i) sequencing the plurality of oligonucleotide fragments to obtain oligonucleotide reads;

j) assembling the oligonucleotide reads; and k) determining the nucleic acid sequence of the assembled oligonucleotide reads to determine the nucleic acid sequence of the polynucleotide.

18. The method of claim 17, wherein a unique barcode sequence is used for each attaching step, and wherein each repeat of the attaching step uses a different unique barcode sequence.

19. The method of claim 17, wherein a single barcode sequence is used for all attaching steps and each repeated collection of step g) is kept separate from the other collections of step g).

20. The method of claim 17, wherein a unique barcode sequence is used for each oligonucleotide sequence and for all attaching steps.

21. The method of claim 17, wherein steps e)-g) are repeated until substantially all of the plurality of oligonucleotide sequences have been cleaved into oligonucleotide fragments.

22. The method of claim 1 wherein the substrate includes a plurality of troughs and each of the plurality of nucleotides is present in a trough.

23. The method of claim 1 wherein each of the plurality of nucleotides is attached to the given attachment point by a ligand-anti-ligand pair, by an antibody-DNA binding protein pair, by ligation to a complementary single stranded region, by a protein or a linkage moiety.

24. The method of claim 1 including an oligonucleotide bound to the substrate at two or more locations of the oligonucleotide sequence and cleaving the oligonucleotide sequence into two oligonucleotide fragments, each of which is bound to a single, discrete location on the substrate.

25. The method of claim 1 wherein the step of collecting the plurality of oligonucleotide fragments includes a flow of fluid containing the oligonucleotide fragment into a microwell or fluidic flow region.

* * * * *